US012344900B2

(12) United States Patent
Shin et al.

(10) Patent No.: US 12,344,900 B2
(45) Date of Patent: Jul. 1, 2025

(54) METHOD FOR DETERMINING IF A TUMOR HAS A MUTATION IN A MICROSATELLITE

(71) Applicant: The Board of Trustees of the Leland Stanford Junior University, Stanford, CA (US)

(72) Inventors: Giwon Shin, Stanford, CA (US); Hanlee P. Ji, Stanford, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 756 days.

(21) Appl. No.: 17/634,223

(22) PCT Filed: Dec. 17, 2020

(86) PCT No.: PCT/US2020/065740
§ 371 (c)(1),
(2) Date: Feb. 9, 2022

(87) PCT Pub. No.: WO2021/127267
PCT Pub. Date: Jun. 24, 2021

(65) Prior Publication Data
US 2022/0316015 A1  Oct. 6, 2022

Related U.S. Application Data

(60) Provisional application No. 62/949,950, filed on Dec. 18, 2019.

(51) Int. Cl.
*C12Q 1/6886* (2018.01)
*C12N 15/10* (2006.01)
*C12Q 1/6869* (2018.01)

(52) U.S. Cl.
CPC .......... *C12Q 1/6886* (2013.01); *C12N 15/10* (2013.01); *C12Q 1/6869* (2013.01); *C12Q 2600/16* (2013.01)

(58) Field of Classification Search
CPC ..... C12Q 1/6886; C12Q 1/6869; C12N 15/10
See application file for complete search history.

(56) References Cited

U.S. PATENT DOCUMENTS 7,902,343 B2    3/2011  Bacher et al.
10,294,529 B2   5/2019  Lambrechts
2016/0362751 A1* 12/2016 Shin ..................... C12Q 1/6869

FOREIGN PATENT DOCUMENTS

WO    WO 2009/012337 A1    1/2009
WO    WO 2016/077553 A1    5/2016
(Continued)

OTHER PUBLICATIONS

Myllykangas et al., Efficient targeted resequencing of human germline and cancer genomes by oligonucleotide-selective sequencing, Nature Biotechnology, 2011, 29, 1024-1027 and online methods (Year: 2011).*

(Continued)

*Primary Examiner* — Cynthia B Wilder
*Assistant Examiner* — Allison E Schloop
(74) *Attorney, Agent, or Firm* — James S. Keddie; Bozicevic, Field & Francis LLP

(57) ABSTRACT

A method for determining if a tumor has a mutation in a microsatellite is provided. In some embodiments, the method may comprise: (a) isolating genomic DNA from a tumor sample and a non-tumor sample from the same patient to produce: i. a sample of tumor DNA and ii. a sample of non-tumor DNA, respectively, (b) without pre-amplifying the tumor or non-tumor DNA, sequencing a plurality of microsatellite loci from both the tumor and non-tumor DNA using OS-seq to provide sequence reads, wherein the sequenced microsatellite loci comprise mononucleotide, (Continued)

dinucleotide, trinucleotide and tetranucleotide microsatellites loci, and (c) comparing the results.

14 Claims, 15 Drawing Sheets

Specification includes a Sequence Listing.

(56) References Cited

FOREIGN PATENT DOCUMENTS

| WO | WO 2018/037231 A1 | 3/2018 |
| WO | WO 2018/175501 A1 | 9/2018 |

OTHER PUBLICATIONS

Jin et al., Similarity/dissimilarity calculation methods of DNA sequences: A survey, Journal of Molecular Graphics and Modelling, 2017, 76, 342-355 (Year: 2017).*

Myllykangas et al., "Efficient targeted resequencing of human germline and cancer genomes by oligonucleotide-selective sequencing", Nat Biotechnol., 1996, 29(11): 1024-1027.

* cited by examiner b a

METHOD FOR DETERMINING IF A TUMOR HAS A MUTATION IN A MICROSATELLITE

CROSS-REFERENCING

This application is a § 371 national phase of International Application No. PCT/US2020/065740, filed on Dec. 17, 2020, which claims the benefit of U.S. provisional application Ser. No. 62/949,950, filed on Dec. 18, 2019, which applications are incorporated by reference herein.

BACKGROUND

Microsatellites (MS) are composed of short tandem repeats (STRs) and are present throughout the human genome. STRs have different classes of motifs that include mono-, di-, tri- and tetranucleotide sequences. In colorectal carcinoma (CRC), somatic mutations or methylation of DNA mismatch repair (MMR) genes (i.e. MSH2, MLH1, PMS2, MSH6) lead to increased mutation rates, particularly in microsatellites. Lynch syndrome is an autosomal dominant genetic disorder in which affected individuals are carriers of deleterious germline mutations in the MMR genes and have a substantially increased risk of CRC, as well as other malignancies. Somatic inactivation of the remaining wildtype allele for a MMR gene leads to inactivation of this DNA repair pathway and increased risk of developing tumors. Tumors with MMR loss display hypermutability in microsatellite sequences. This phenomenon is referred to as microsatellite instability (MSI) and is characterized by the accrual of insertions or deletions (indels) in either coding or non-coding microsatellite sequences. Based on specific criteria, tumors with high levels of microsatellite mutations are referred to as MSI-high (MSI-H), with mutation rates that are orders of magnitude greater than what is observed in tumors that are microsatellite stable (MSS) [1]. Importantly, MSI occurs in all classes of microsatellite repeats. However, nearly all published studies have exclusively focused on the presence of microsatellite mutations within mono- and dinucleotide repeats to assess MSI. Generally, there has not been a careful examination of other microsatellite classes, potentially missing important features of MSI and their underlying genetic complexity of these tumors.

There are a number of methods used for detecting MSI in cancer. One approach involves immunohistochemistry (IHC) staining of tumor sections for MMR protein expression of MLH1, MSH2, MSH6 and PMS2. A tumor lacking expression of one of these proteins is considered to have MSI. The most common molecular genetic assay for identifying MSI-H tumors requires PCR amplification of a limited panel of microsatellite markers. The MSI PCR test uses a multiplexed amplicon assay which requires testing five or more microsatellite markers—typically these are either mono- or dinucleotide repeats [2, 3]. Using capillary electrophoresis (CE), tumor-specific changes in the microsatellite amplicon size indicate MSI when compared to the microsatellite genotypes from matched non-tumor cells. If a sufficient number of microsatellites demonstrate an allelic shift in size (e.g. two or more), the tumor is classified as MSI-H. MSI PCR testing is considered to be the gold standard test for MSI-H. In comparison, MMR IHC misses approximately 10% of tumors with MSI [4, 5]. Despite their diagnostic status, MSI PCR tests have a number of issues. PCR amplification leads to artifacts related to additional indels in microsatellites. This artifact is referred to as a stutter and complicates the identification of MSI, particularly when i) the change in a microsatellite allele occurs in a smaller fraction of the cells, and ii) the allelic shift in size is less than 3 bp.

Next generation sequencing (NGS) approaches for detecting MSI are based on targeted assays that enrich or amplify exon sequences (e.g. exomes and gene panels) or microsatellites [6-10]. When using targeted sequencing with gene panels and exomes, the presence of indels within exon-based mono- or dinucleotide repeats determines MSI status. Sequencing demonstrates the presence of mutations within micro satellite tracts, leading to allelic shifts and new genotypes. Generally, MSI NGS assays have high concordance with MSI PCR tests [6, 8-10]. However, MSI NGS tests are also susceptible to artifacts related to sequencing library amplification. PCR amplification stutter is also seen in all MSI NGS tests. Therefore, detection of MSI when tumor cellularity is at a low fraction remains a challenge for NGS detection.

The conventional criteria for defining MSI is restricted to mono- or dinucleotide repeats. However, there is another category of instability that involves elevated microsatellite alterations at selected tetranucleotide repeats (EMAST). This category of microsatellite alterations is thought to be related to changes in the function of MSH3, another gene of the MMR pathway. MSH3 loss of function is characterized by instability in dinucleotide or longer repeats [11]. CRCs with EMAST have been reported in up to 50% of tumors; they are driven by changes in a variety of pathways that lead to genome instability (e.g., MSI, CpG island methylator phenotype, etc.) [11]. The EMAST phenotype may be associated with an elevated microsatellite mutation rate of mono- and dinucleotide repeats, but this is not consistently observed [12-15]. EMAST CRCs are also frequently associated with chromosomal instability (CIN) where portions of the genome show copy number alterations, aneuploidy and rearrangements [11]. However, there are few if any genomic studies that have examined these EMAST CRCs in greater genomic detail. Furthermore, there are no reports of EMAST tumors analyzed with whole genome sequencing (WGS).

Detection of EMAST involves testing a set of tetranucleotide microsatellites for instability changes. The most common method involves PCR genotyping assays analyzed with capillary electrophoresis [12]. Currently, there are no established markers or criteria which are used in classifying EMAST [16]. Recent studies have relied on using five or more tetranucleotide markers; a tumor is considered to be EMAST positive when 30% or more of the markers are unstable compared to the matched normal DNA genotypes [12-15]. NGS methods for detecting EMAST are generally not available, seeing that most targeting assays do not include microsatellites, such as tetranucleotide repeats [6-9]. Generally, exons lack tetranucleotide repeats of sufficient length and as a result, exome or targeted gene sequencing will miss these genomic instability features. Targeted sequencing assays with short reads may span the entire length of tetra-nucleotide microsatellites, which are frequently longer than mono- and dinucleotide repeats.

Determining the MSI status of CRCs and other tumors is of increasing importance given advances in cancer immunotherapy. MSI-related indels in exons produce frameshift mutations within a gene, leading to a higher number of novel peptides, also referred to as neopeptides, from the translated mutated protein. For MSI-H cancers, these neopeptides provide an abundance of unique cancer antigens that are absent from normal colon and rectal cells. Pembrolizumab and other immune checkpoint drugs stimulate the immune system such that T cells recognize these highly immunogenic cancer cells and their cancer-related neoantigens [17]. Thus, the patient mounts an immune response against his or her own cancer. Given the therapeutic predictive nature of MSI status for immunotherapy, molecular genetic testing is a diagnostic requirement for receiving immune checkpoint therapies. Surprisingly, even for MSI-H tumors anywhere from 10 to 40% do not show a response and despite improvements in progression free survival, up to one third of patients with MSI-H tumors continue to grow and lead to death [17-19]. Therefore, it remains an open question as to why a significant proportion of MSI-H tumors do not respond or progress while on immune checkpoint therapy.

As noted, nearly all studies determining the presence of MSI in CRCs examine only mono- and dinucleotides. The same holds true for other cancer types with MSI [20]. Limiting the evaluation of MSI to only two classes of microsatellites overlooks more complex genetic features, such as instability in tetranucleotide repeats. Addressing this gap in knowledge about cancer mutations in microsatellites, a new sequencing approach to profile instability across different classes of microsatellites and cancer genes was developed. The analysis included an expanded set of mono-, di-, tri- and tetranucleotide repeats with minimal amplification error and high read coverage. Ultra-depth sequencing coverage in the thousands was used for sensitive detection of somatic events. These features identify somatic microsatellite and gene mutations with high accuracy. Thus, one can quantify genomic changes that are indicative of genetic heterogeneity and subclonal diversity present in a given tumor. Simultaneously, chromosomal instability (CIN) was detected via the high-accuracy identification of copy number alterations in cancer genes.

Diverse microsatellite types were profiled while considering additional features of genomic instability that may affect cancer driver genes. As demonstrated on a cohort of CRCs, this approach provided sensitive detection of MSI, generated quantitative microsatellite profiles informative for EMAST, revealed mixed classes of chromosomal instability and delineated genetic heterogeneity with subclonal structure. The profiling results showed that some colorectal cancers have both MSI and CIN co-occurrence. To further characterize the extent of chromosomal changes, WGS was conducted on tumors with mixed genome instability features. Whole genome analysis confirmed the findings from the targeted approach and showed evidence of inter-chromosomal rearrangements in MSI CRCs. The results may have potential clinical implications in how MSI CRCS are evaluated for immunotherapy.

The following approach is believed to address at least some of the issues set forth above.

SUMMARY

To address aforementioned issues, a new approach has been developed for jointly evaluating different types of microsatellites and chromosomal instability, seen in copy number alterations. In some embodiments, the method is for determining if a tumor has a mutation in a microsatellite. In these embodiments, the method may comprise: (a) isolating genomic DNA from a tumor sample and a non-tumor sample from the same patient to produce: i. a sample of tumor DNA and ii. a sample of non-tumor DNA, respectively; (b) without pre-amplifying the tumor or non-tumor DNA, sequencing a plurality of microsatellite loci from both the tumor and non-tumor DNA to provide sequence reads, wherein the sequenced microsatellite loci comprise mononucleotide, dinucleotide, trinucleotide and tetranucleotide microsatellites loci; (c) analyzing the sequence reads of (b) by: (i) determining a first profile of read counts across n alleles of a selected microsatellite locus in the tumor DNA (wherein n may be in the range of 4-20); and (ii) calculating the difference between the first profile of (i) and a second profile of read counts across n alleles for the selected microsatellite locus in the non-tumor DNA; and (iii) comparing the calculated difference to a threshold; and (d) designating the tumor as having mutation in the selected microsatellite locus if the difference of (ii) is equal to or above the threshold.

This method analyzes mono- and dinucleotide repeats sequenced with high accuracy and minimal amplification error. Importantly, features of other classes of sequence tandem repeats including tri- and tetranucleotide repeats are included. As demonstrated, the present method provides a new approach towards highly sensitive detection of MSI, cancer mutations and other genetic aberrations in parallel. The current PCR and NGS tests for MSI do not show the full spectrum of this molecular phenotype and sometimes misses tumors with MSI. Moreover, the new approach quantitatively measures MSI intensity from a more expansive set of microsatellites as well as detecting other categories of genetic aberrations indicative of chromosomal instability. Using a cohort of 46 CRC patients, the tumors' genetic diversity was studied. With validations using conventional methods, it has been shown that the assay can correctly categorize CRC tumors in terms of mutation abundance in more than 200 microsatellites as well as degree of genome-wide instability in copy numbers. Moreover, a multi-categorical classification of CRC tumors, with which better prediction of response to immune check point drugs may be possible, is suggested.

BRIEF DESCRIPTION OF THE DRAWINGS

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
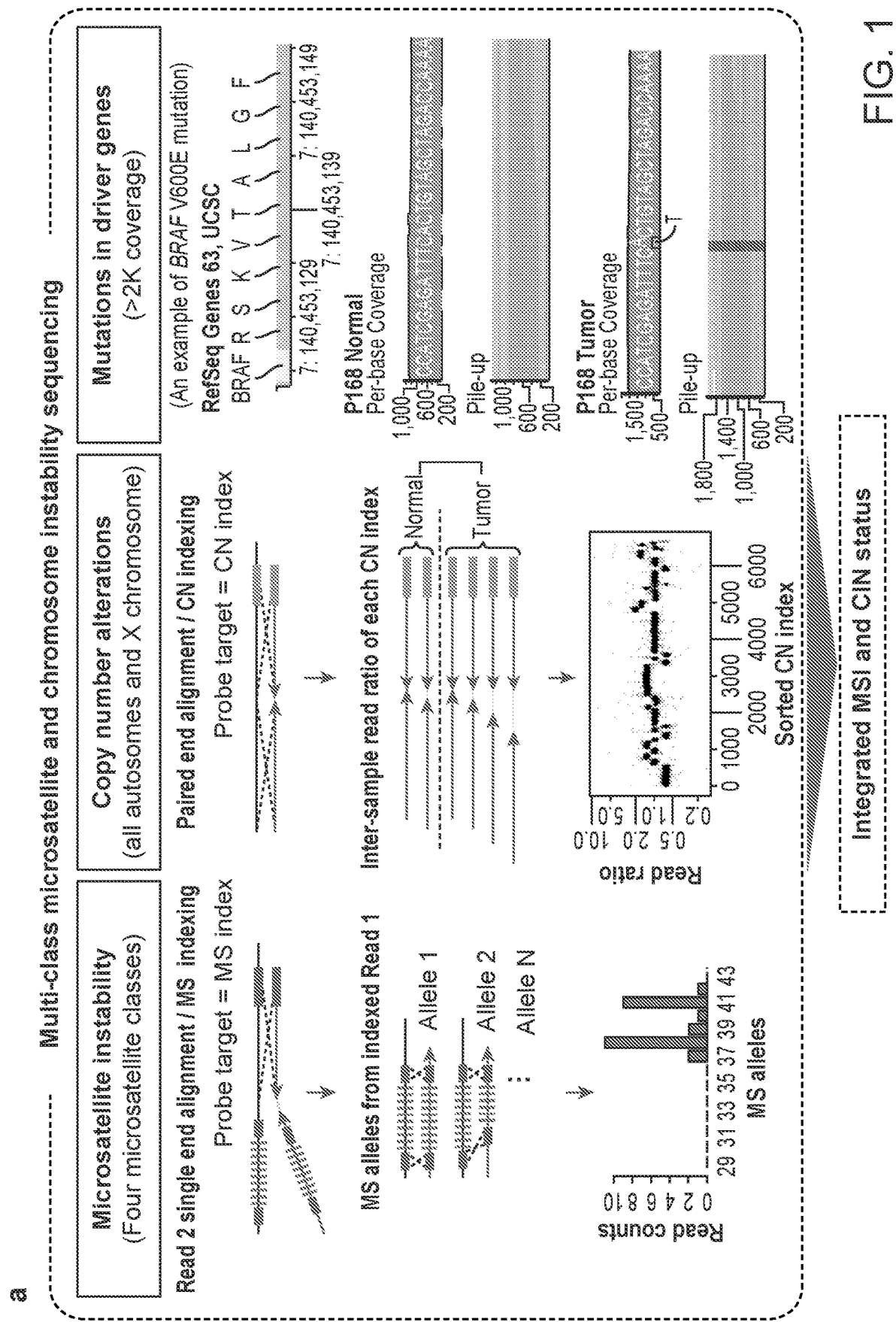
FIG. 1 *a* provides an integrated sequencing-based determination of microsatellite and chromosomal instabilities. An overview of the sequencing analysis that simultaneously determines microsatellite instability (MSI) and chromosomal instability (CIN) are shown. Mutations in driver genes also provide supplementary information that further supports the integrated determination. To determine MSI status based on four classes of microsatellites (mono-, di-, tri-and tetranucleotide repeats), after single end alignment of Read 2 sequences, the reads are indexed if aligning on target. The indexing informs the repeat motif and flanking non-repeat sequences, which are expected to be sequenced in the corresponding Read 1 sequence. Reads are counted for every observed microsatellite allele (i.e. number of motif repetition), and generate a histogram, of which the comparison between tumor versus normal samples determines somatic microsatellite mutation. To determine CIN status, copy number alterations are analyzed. After paired end alignment, the reads are indexed if aligning on target. An inter-sample comparison of read counts sharing the same index determines copy number alteration if the ratio is unusually high or low compared to the average ratio from all the indexes. Additionally, the targets for copy number analysis are also well-known driver genes. The ultra-deep PCR-free targeted sequencing enables sensitive and quantitative detection of pathogenic mutations, and the mutation profile matching the molecular subtype improves validity of the methods. Shown here is an examples of BRAF V600E mutation detected from a MSI tumor. SEQ ID NOS: 1 and 2.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. The nucleic acid samples used herein may be complex in that they contain multiple different molecules that contain sequences. Genomic DNA and cDNA made from mRNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, cDNA (from RNA) or artificial DNA constructs. Any sample containing nucleic acid, e.g., genomic DNA made from tissue culture cells, a sample of tissue, or an FFPE sample, may be employed herein.

The term "nucleic acid sample," as used herein denotes a sample containing nucleic acids. A nucleic acid sample used herein may be complex in that they contain multiple different molecules that contain sequences. Genomic DNA, RNA (and cDNA made from the same) from a mammal (e.g., mouse or human) are types of complex samples. Complex samples may have more then $10^4$, $10^5$, $10^6$ or $10^7$ different nucleic acid molecules. A target molecule may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., peptide nucleic acid or PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylenecarbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotides of from about 2 to 200 nucleotides, or up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18 to 40, 20 to 35, 21 to 30 nucleotides long, and any length between the stated ranges. Typical primers can be in the range of between 10 to 50 nucleotides long, such as 15 to 45, 18 to 40, 20 to 30, 21 to 25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "genomic region", as used herein, refers to a region of a genome, e.g., an animal or plant genome such as the genome of a human, monkey, rat, fish or insect or plant.

The term "terminal nucleotide", as used herein, refers to the nucleotide at either the 5' or the 3' end of a nucleic acid strand. The nucleic acid strand may be in double-stranded (i.e., duplexed) or in single-stranded form.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that at least partly complementary to the "top strand." When an oligonucleotide binds or anneals "only to one strand," it binds to only one strand, e.g., the first or second strand, but not the other strand. In certain cases and as will be described in greater detail below, two strands may be annealed to one another in a duplex but there may be part of the duplex that is not annealed (e.g., because the sequences are not complementary). In these cases, the strands that are not annealed may still be referred to as being "top" and "bottom" strands because they are covalently linked to strands that are annealed to one another.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired.) Nucleic acid may also be denatured chemically (e.g., using urea or NaOH).

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a unique sequence of nucleotides used to (a) identify and/or track the source of a polynucleotide in a reaction and/or (b) count how many times an initial molecule is sequenced (e.g., in cases where substantially every molecule in a sample is tagged with a different sequence, and then the sample is amplified). A barcode sequence may be at the 5'-end, the 3'-end or in the middle of an oligonucleotide, or both the 5' end and the 3' end. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "target nucleic acid" as use herein, refers to a polynucleotide of interest under study.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

As used herein, the term "short tandem repeat" refers to a microsatellite repeat, composed of a unit of two to thirteen nucleotides repeated up to hundreds of times (usually 5-50 times) in a row in genomic DNA. The number of tandem repeats at any STR locus may vary from individual to individual. STR analysis measures the exact number of repeating units in a locus. See, e.g., Richard et al. (Micr. Mol. Bio. Rev 2008 72: 686-727).

Figure 9:
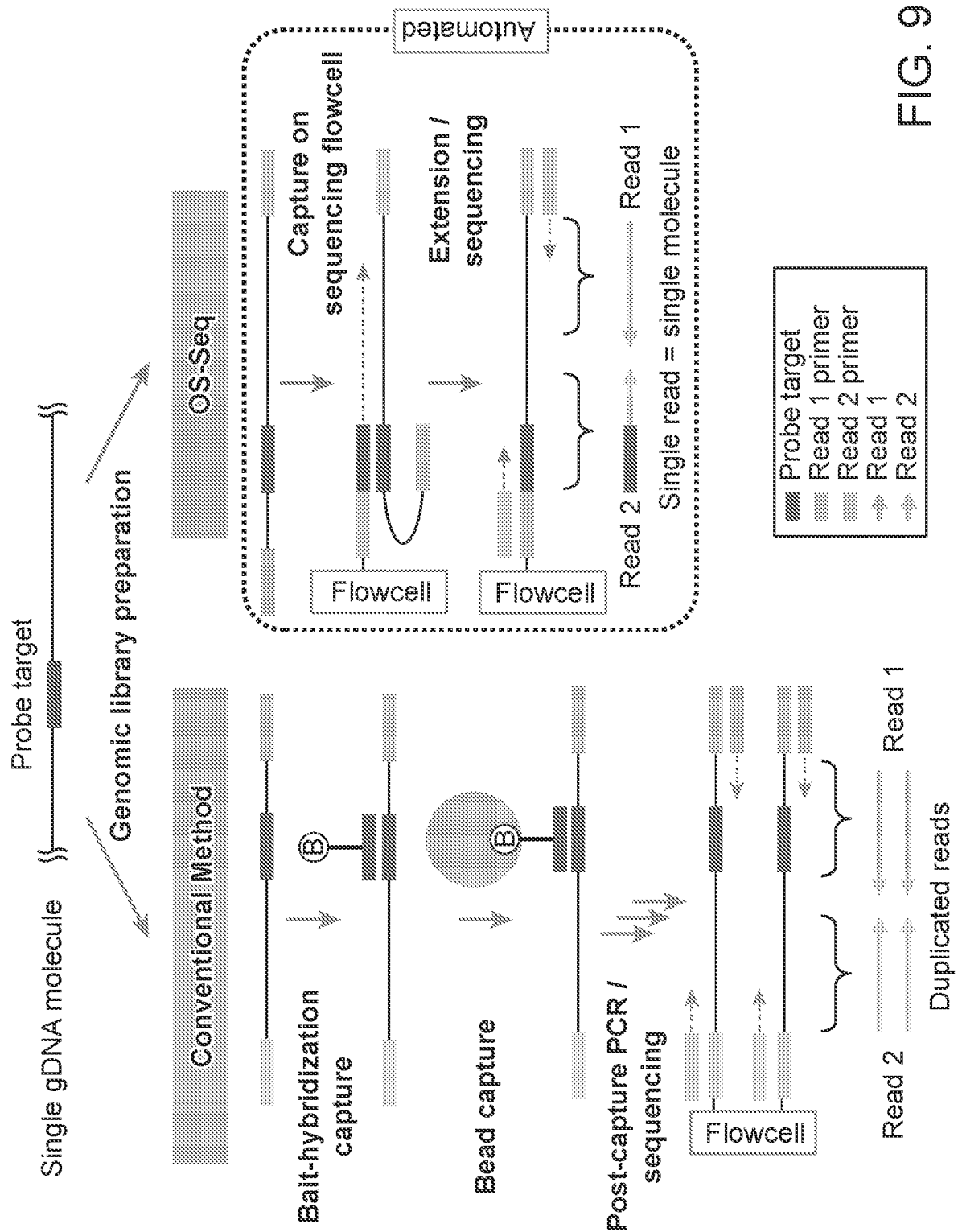
FIG. 9 a-b provides comparison between conventional and single primer targeted sequencing methods. The single primer-targeted sequencing method used in the current study (OS-Seq) is compared with a conventional method, generally used for the whole exome and gene panels. This single primer targeting method uses a single adapter library, while the conventional method uses a ready-to-sequence dual-adapter library. The capture process itself completes the libraries for the subsequent sequencing step. Steps for targeting genomic sequence involves a round of hybridization and single primer extension. This process is simpler compared to the conventional method which generally uses multiple wash steps after immobilizing the captured library with magnetic beads. Moreover, targeted sequencing is easily automated with a commercial system (e.g. Illumina cBot). Most importantly, OS-Seq requires no post capture PCR step when using capture probes already immobilized on the sequencing flowcell. Therefore, a sequencing read represents a single DNA molecule. PCR-born indels, or stutters can be minimized especially when targeting microsatellites.

The term "OS-seq" is used to refer to the method described in U.S. Pat. No. 9,309,556, Myllykangas (Nat Biotechnol. 2011 29: 1024-7) and Hopmans et al (Nucleic Acids Res 2014 42: e88) and comprises: (a) capturing fragments comprising the target loci (e.g., the selected microsatellite loci) on a flow cell by hybridization to oligonucleotides that are tethered to the flow cell; (b) copying the complements of the sequences of the target loci onto the ends of the oligonucleotides to produce flow cell-tethered primer extension products; and (c) sequencing the flow cell-tethered primer extension products on the flow cell using reversible terminators (i.e., by Illumina sequencing). The OS-seq method is illustrated in FIG. 9.

DETAILED DESCRIPTION

Provided herein is a method for determining if a tumor has a mutation in a microsatellite. In some embodiments, the method may comprise isolating genomic DNA from a tumor sample and a non-tumor sample from the same patient to produce: i. a sample of tumor DNA and ii. a sample of non-tumor DNA, respectively.

For example, genomic DNA may be isolated from a tissue biopsies, surgical resections or aspirates, etc., where one of the samples contains tumor cells and the other does not contain tumor cells. In some embodiments, multiple sample types or multiple regions from the same sample type may be analyzed. In these embodiments, the term "tissue section" refers to a piece of tissue that has been obtained from a subject and optionally fixed. Biopsies of interest include both tumor and non-neoplastic biopsies of skin (melanomas, carcinomas, lymphomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc. In some embodiments, the method may be performed on cancers for which a treatment by immunotherapy exists. For example, the tumor sample used the method may be a sample of melanoma, lung cancer, breast cancer, head and neck cancer, bladder cancer, Merkel cell cancer, cervical cancer, hepatocellular cancer, gastric cancer, cutaneous squamous cell cancer, classic Hodgkin lymphoma, B-cell lymphoma, colorectal carcinoma, pancreatic carcinoma, gastric or breast carcinoma. The sample may be for example, a fresh frozen sample or a fixed sample such as a formalin-fixed paraffin embedded (FFPE) sample, unless the genomic DNA is too degraded. In some embodiments, the genomic DNA may be fragmented before employing it in the present method. Adapters may be ligated onto the ends of the isolated genomic DNA of both samples. In many cases, the adapters may contain a sample barcode, thereby allowing the tumor and non-tumor samples to be combined with one another and with other samples.

Next, without pre-amplifying the tumor or non-tumor DNA (i.e., without amplifying the DNA by solution-phase PCR), the method comprises sequencing a plurality of microsatellite loci from both the tumor and non-tumor DNA, wherein the plurality of microsatellite loci comprises mononucleotide, dinucleotide, trinucleotide and tetranucleotide microsatellites loci. This step may be done by enriching for the microsatellite fragments by target enrichment (as shown in FIG. 9) and then directly applying the captured fragments to a flow-cell where the fragments are sequenced. The primer extension products can then be sequenced, without in-solution amplification, to provide sequence reads. This method, in which the fragments are captured, copied and then sequenced on a support is illustrated in FIG. 9. In alternative embodiments, this step may be done using a technique called "OS-seq", which involves capturing nucleic acid plurality of microsatellite loci by hybridization to primers that are immobilized by their 5 ends on a solid support, extending the primers to provide copies of the microsatellite loci that are immobilized on the solid support, and sequencing the copy (i.e., the primer extension product) on the support, e.g., by Illumina sequencing. This technique is described in greater detail in U.S. Pat. No. 9,309,556, Myllykangas (Nat Biotechnol. 2011 29: 1024-7) and Hopmans et al (Nucleic Acids Res 2014 42: e88), which are incorporated by reference herein. In some embodiments, the loci may be copied prior to sequencing, where the copying step may be done by annealing primers one side of the microsatellite loci (one primer per microsatellite locus) and then extending the primers, thereby copying the microsatellite loci. As noted above, this method does not involve in-solution amplification (i.e., is PCR-free) although, in some embodiments, the fragments may be amplified on the sequencing substrate.

The sequence reads may be analyzed by comparing, for each microsatellite, profiles of read counts across multiple alleles (e.g., at least 5, at least 10, at least 15 or at least 20) where, in the context of this disclosure, an allele can corresponds to a number of repeats in a microsatellite. Visually, this may be shown as a bar graph showing the number of sequence (i.e., the read count) for each potential microsatellite allele, as shown in FIG. 1. The number alleles analyzed may vary greatly and, in some embodiments, may be in the range of 4-20. In some embodiments, this step of the method may involve: (i) determining a first profile of read counts across n alleles (wherein n may be in the range of 4-20, for example) of a selected microsatellite locus in the tumor DNA and (ii) calculating the difference between the that profile a second profile of read counts across n alleles for the selected microsatellite locus in the non-tumor DNA. This latter step may be done mathematically using any convenient method. For example, this calculating step may comprise calculating the Euclidean distance between the first profile of read counts and the second profile of read counts. This part of the method is illustrated by example in FIG. 8 a. In this example, a profile of read counts is determined for the tumor and non-tumor samples, and the distance between the profiles can be calculated.

In this method, the calculated difference in read counts be comparing to a threshold, and the tumor may be designated as having mutation in the selected microsatellite locus if the difference of (ii) is equal to or above the threshold. Any threshold used in the method may be established empirically. In some embodiments, steps (i) and (ii) can be repeated for all of the sequenced microsatellite loci and, in these embodiments, the method may determining the number of microsatellite loci that have a mutation in the tumor DNA, thereby providing a measure of microsatellite instability in the tumor. As noted above, cancers that are associated with microsatellite instability appear to be more susceptible to immunotherapy. A such, in some embodiments, the method may comprise (i) identifying the patient as having a level of microsatellite instability that is above a threshold; and (ii) administering immunotherapy to the patient. In some embodiments, the immunotherapy may an immune checkpoint inhibitor, e.g., an antibody, e.g., an anti-CTLA-4 antibody, anti-PD1 antibody, an anti-PD-L1 antibody, an anti-TIM-3 antibody, an anti-VISTA antibody, an anti-LAG-3 antibody, an anti-IDO antibody, or an anti-KIR antibody, although others are known. In some embodiments, the immunotherapy may also include a co-stimulatory antibody such as an antibody against CD40, GITR, OX40, CD137, or ICOS, for example. In some embodiments, the antibody may be an anti-PD-1 antibody, an anti-PD-L1 antibody or an anti-CTLA-4 antibody. Examples of such antibodies include, but are not limited to: Ipilimumab (CTLA-4), Nivolumab (PD-1), Pembrolizumab (PD-1), Atezolizumab (PD-L1), Avelumab (PD-L1), and Durvalumab (PD-L1). These therapies may be combined with one another with other therapies. In some embodiments, the dose administered may be in the range of 1 mg/kg to 10 mg/kg, or in the range of 50 mg to 1.5 g every few weeks (e.g., every 3 weeks), depending on the weight of the patient. In certain embodiments, the patient will be treated with the immune checkpoint inhibitor without knowing the PD1, CTLA-4, TIM-3, VISTA, LAG-3, IDO or KIR status of the tumor.

In some embodiments, the method may comprise sequencing at least 100 microsatellite loci (e.g., at least 150 or at least 200 microsatellite loci) from both the tumor and non-tumor DNA.

In some embodiments, the sequencing step of the method may comprise without pre-amplifying the tumor or non-tumor DNA, sequencing a plurality of unique non-microsatellite loci from both the tumor and non-tumor DNA to provide sequence reads, wherein the unique non-microsatellite loci comprise loci from all chromosomes; and the analysis step may further comprise analyzing the sequence reads of a selected unique non-microsatellite locus by: (i) calculating the ratio (e.g., a normalized log 2 ratio, for example) of the total number of read counts for the selected unique non-microsatellite locus in the tumor DNA relative to the total number of read counts for the selected unique non-microsatellite locus in the non-tumor DNA; and (ii) comparing the ratio to a threshold. In these embodiments, the method may further comprises designating the tumor as having chromosomal instability the ratio of (i) is equal to or above the threshold. In any embodiment, sequencing may be done by paired end sequencing. In these embodiments, the sequence reads compared in the method are read 2 sequences.

In some embodiments, the method may comprise providing a report indicating whether there is microsatellite instability, or a score based on the foregoing analysis that indicates the same. Such a score may be numerical or alphabetical, or may use descriptors such as "high", "medium" or "low", or symbols such as "+++", "++", "+" or "−", for example). In some embodiments, a report may provide options for approved (e.g., FDA approved) therapies, e.g., immune checkpoint inhibitors, for cancers that are associated with the analysis, particularly if the mutation(s) identified in the sample are also known. This information can guide treatment decisions made by a physician, In some embodiments, the report may be in an electronic form, and the method comprises forwarding the report to a remote location, e.g., to a doctor or other medical professional to help identify a suitable course of action, e.g., to identify a suitable therapy for the subject. The report may be used along with other metrics to determine whether the subject may be susceptible to immune checkpoint inhibition.

In any embodiment, a report can be forwarded to a "remote location", where "remote location," means a location other than the location at which the sequences are analyzed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet, including email transmissions and information recorded on websites and the like. In certain embodiments, the report may be analyzed by an MD or other qualified medical professional, and a report based on the results of the analysis of the sequences may be forwarded to the patient from which the sample was obtained.

As would be readily appreciated, many steps of the method, e.g., the sequence processing steps and analysis steps may be implemented on a computer. As such, in some embodiments, the method may comprise executing an algorithm that performs the analysis steps.

In computer-related embodiments, a system may include a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions for providing a score using the measurements described above as inputs. The computer processor is coupled to the storage component and configured to execute the instructions stored in the storage component in order to receive patient data and analyze patient data according to one or more algorithms. The display component may display information regarding the diagnosis of the patient.

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the diagnostic system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In order to further illustrate the present invention, the following specific examples are given with the understanding that they are being offered to illustrate the present invention and should not be construed in any way as limiting its scope.

Examples

The following examples are given for the purpose of illustrating various embodiments of the invention and are not meant to limit the invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Materials and Methods

Cancer Samples

This study was conducted in compliance with the Helsinki Declaration. All patients were enrolled according to a study protocol approved by the Stanford University School of Medicine Institutional Review Board (IRB-11886 and IRB-48492). Informed consent was obtained from all patients. Tissues were obtained from the Stanford Cancer Institute Tissue bank as well as the Netherland Cancer Institute.

Matched tumor and normal specimens underwent histopathology review to mark areas of tumor and normal tissue on hematoxylin and eosin-stained tissue sections and on the corresponding paraffin blocks. The samples were generally 60% tumor purity or higher. The samples were macro-dissected to provide improved tumor purity and extracted genomic DNA from the matched normal and tumor CRC samples. The dissected tissue was homogenized and processed using the E.Z.N.A. SQ RNA/DNA/Protein Extraction Kit (Omega Biotek Inc.). Briefly, the cells were lysed using provided lysis buffer (SQ1); proteins were precipitated and removed with protease (SQ2) and NaOAc; nucleic acids were precipitated with isopropanol; washed; and nucleic acid pellets were re-suspended in 10 mM Tris-HCl (pH 8.0) buffer. RNA species in the nucleic acid were removed via the addition of 4 µg of RNase A (Promega), and incubation at 37° C. for 1 hour. After incubation, each sample was purified with AMPure XP beads in a bead solution-to-sample ratio of 1.5. Nucleic acids were quantified pre- and post-RNase treatment using a Thermo Scientific NanoDrop™ 8000 spectrophotometer or Qubit Broad Range DNA kit (Thermo Fisher Scientific). In addition, some genomic DNA was obtained from punched tissue cores using Maxwell FFPE tissue LEV DNA purification kit (Promega) per the manufacturer's guidelines and quantitated based on the same protocol as described.

Joint Sequencing of Microsatellites and Cancer Genes

A targeted sequencing technology which provides ultra-deep coverage and enables amplification-free libraries with reduced PCR error was adapted (FIG. 1a) [21-23]. Referred to as oligonucleotide-selective sequencing (OS-Seq) this assay uses only a single primer, also called primer probe, that anneals to a target sequence and as a result avoids issues found with traditional PCR or bait-hybridization enrichment of target exons. Extension from the target-specific primer copies the target sequence in massively multiplexed fashion. Primer probes for 225 microsatellite markers and 1,387 exons from 85 genes were designed (Table 1). The microsatellites included diverse sequence tandem repeat motifs (Table 2). These primers include mono-and dinucleotide repeats, as well as tri-and tetranucleotide repeats; the broader representation of motifs allowed us to distinguish different types of MSI, including those markers used for MSI PCR testing and EMAST. Using results from the Cancer Genome Atlas project, the cancer genes with the highest frequency of mutations present in colorectal and gastric cancer were selected [1, 24]. The targeted exons from 85 genes were located across all autosomal and X chromosomes (Table 3).

TABLE 1

|  | Target (#) | Primer probe (#) | Total target size (kb) |
| --- | --- | --- | --- |
| Gene/exon | 85/1387 | 5849 | 384.5 |
| Mono- and dinucleotide repeats | 181 | 368 | 20 |
| Tri- and tetranucleotide repeats | 44 | 88 | 6.7 |
| Total | 1612 | 6305 | 411.2 |

TABLE 2

| STR ID | Chr | Start (0-base) | End (1-base) | hg19 length | Motif | Gene location |
| --- | --- | --- | --- | --- | --- | --- |
| D1GATA113 | 1 | 7442890 | 7442934 | 44 | GATA | CAMTA1_intron |
| PRDM2 | 1 | 14108748 | 14108757 | 9 | A | PRDM2_exon |
| EPHB2 | 1 | 23239994 | 23240001 | 7 | A | EPHB2_exon |
| TCEB3 | 1 | 24078403 | 24078411 | 8 | A | TCEB3_exon |
| WDTC1 | 1 | 27621107 | 27621115 | 8 | G | WDTC1_exon |
| nc-HEJ1 | 1 | 102358806 | 102358816 | 10 | A | OLFM3_intron |
| D1S1627 | 1 | 106963713 | 106963752 | 39 | ATT | intergenic |
| SYCP1 | 1 | 115537600 | 115537610 | 10 | A | SYCP1_exon |
| BAT40 | 1 | 120053335 | 120053377 | 42 | T | HSD3B1_intron |
| RFX5 | 1 | 151318740 | 151318747 | 7 | G | RFX5_exon |
| NTRK1 | 1 | 156836726 | 156836734 | 8 | TC | NTRK1_exon |
| AIM2 | 1 | 159032486 | 159032496 | 10 | T | AIM2_exon |
| D1S1677 | 1 | 163559815 | 163559875 | 60 | TTCC | intergenic |
| F13B | 1 | 197007831 | 197007859 | 28 | TAAA | intergenic |
| MDM4 | 1 | 204518354 | 204518362 | 8 | TC | MDM4_exon |
| PCNXL2 | 1 | 233388512 | 233388519 | 7 | T | PCNXL2_exon |
| TPOX | 2 | 1493424 | 1493456 | 32 | AATG | TPO_intron |
| TAF1B | 2 | 9989570 | 9989581 | 11 | A | TAF1B_exon |
| MAPRE3 | 2 | 27248516 | 27248524 | 8 | C | MAPRE3_exon |
| MSH2 | 2 | 47639587 | 47639594 | 7 | A | MSH2_exon |
| BAT26 | 2 | 47641559 | 47641586 | 27 | A | MSH2_intron |
| MSH6_1 | 2 | 48025856 | 48025863 | 7 | A | MSH6_exon |
| MSH6_2 | 2 | 48030639 | 48030647 | 8 | C | MSH6_exon |
| D2S123 | 2 | 51288512 | 51288554 | 42 | CA | intergenic |
| nc-IL1R2 | 2 | 102626435 | 102626443 | 8 | C | IL1R2_intron |
| SLC35F5 | 2 | 114500276 | 114500286 | 10 | A | SLC35F5_exon |
| GRB14 | 2 | 165365287 | 165365296 | 9 | T | GRB14_exon |
| D2S1776 | 2 | 169645402 | 169645446 | 44 | AGAT | NOSTRIN_intron |
| nc-BMPR2 | 2 | 203427559 | 203427570 | 11 | A | BMPR2_UTR |
| D2S1338 | 2 | 218879581 | 218879673 | 92 | GGAA | intergenic |
| SLC4A3_1 | 2 | 220494110 | 220494117 | 7 | C | SLC4A3_exon |
| SLC4A3_2 | 2 | 220502412 | 220502419 | 7 | C | SLC4A3_exon |
| nc-CMTM6 | 3 | 32522862 | 32522872 | 10 | A | CMTM6_UTR |
| MLH1 | 3 | 37059065 | 37059073 | 8 | AC | MLH1_exon |
| CTNNB1 | 3 | 41278163 | 41278171 | 8 | CT | CTNNB1_exon |
| D3S1358 | 3 | 45582240 | 45582292 | 52 | TATC | LARS2_intron |
| nc-GNL3 | 3 | 52728312 | 52728322 | 10 | T | GNL3_UTR |
| D3S4529 | 3 | 85751008 | 85751060 | 52 | AGAT | CADM2_intron |
| RG9MTD1 | 3 | 101284008 | 101284018 | 10 | A | TRMT10C_exon |
| ZBTB20 | 3 | 114058002 | 114058009 | 7 | G | ZBTB20_exon |
| MBD4 | 3 | 129155547 | 129155557 | 10 | T | MBD4_exon |
| ASTE1 | 3 | 130733046 | 130733057 | 11 | T | ASTE1_exon |
| PIK3CB_1 | 3 | 138382755 | 138382762 | 7 | T | PIK3CB_exon |
| PIK3CB_2 | 3 | 138413709 | 138413716 | 7 | G | PIK3CB_exon |
| ATR | 3 | 142274739 | 142274749 | 10 | T | ATR_exon |
| nc-KPNA4 | 3 | 160219060 | 160219105 | 45 | A | KPNA4_UTR |
| D3S3053 | 3 | 171750964 | 171751000 | 36 | GATA | intergenic |
| PIK3CA | 3 | 178919193 | 178919200 | 7 | A | PIK3CA_exon |
| nc-NDUFB5 | 3 | 179344053 | 179344067 | 14 | T | NDUFB5_UTR |
| ABCC5 | 3 | 183665256 | 183665265 | 9 | A | ABCC5_exon |
| FGFR3 | 4 | 1806180 | 1806187 | 7 | C | FGFR3_exon |
| C4orf6 | 4 | 5527115 | 5527125 | 10 | T | C4orf6_exon |
| D4S2408 | 4 | 31304419 | 31304455 | 36 | ATCT | intergenic |
| nc-APBB2 | 4 | 41034523 | 41034531 | 8 | G | APBB2_intron |

TABLE 2-continued

| STR ID | Chr | Start (0-base) | End (1-base) | hg19 length | Motif | Gene location |
|---|---|---|---|---|---|---|
| PDGFRA | 4 | 55161350 | 55161358 | 8 | AG | PDGFRA_exon |
| BAT25 | 4 | 55598197 | 55598236 | 39 | T | KIT_intron |
| KDR | 4 | 55953854 | 55953862 | 8 | AG | KDR_exon |
| CLOCK | 4 | 56336953 | 56336962 | 9 | A | CLOCK_exon |
| D4S2364 | 4 | 93517372 | 93517400 | 28 | ATTC | GRID2_intron |
| EGF_1 | 4 | 110880510 | 110880518 | 8 | TG | EGF_exon |
| EGF_2 | 4 | 110883116 | 110883124 | 8 | GA | EGF_exon |
| EGF_3 | 4 | 110890158 | 110890166 | 8 | AG | EGF_exon |
| LARP7 | 4 | 113570753 | 113570761 | 8 | A | LARP7_exon |
| FBXW7 | 4 | 153253762 | 153253770 | 8 | TC | FBXW7_exon |
| FGA | 4 | 155508887 | 155508975 | 88 | AAAG | FGA_intron |
| TERT | 5 | 1294664 | 1294671 | 7 | G | TERT_exon |
| trf661147 | 5 | 58698968 | 58699000 | 32 | AGAC | PDE4D_intron |
| PIK3R1 | 5 | 67522740 | 67522747 | 7 | A | PIK3R1_exon |
| MSH3 | 5 | 79970914 | 79970922 | 8 | A | MSH3_exon |
| D5S346 | 5 | 112213678 | 112213718 | 40 | TG | REEP5_UTR |
| D5S818 | 5 | 123111249 | 123111293 | 44 | ATCT | intergenic |
| RAD50 | 5 | 131931451 | 131931460 | 9 | A | RAD50_exon |
| PCDHGA12 | 5 | 140812775 | 140812787 | 12 | T | PCDHGA12_exon |
| CSF1PO | 5 | 149455886 | 149455938 | 52 | ATCT | CSF1R_intron |
| D6S1017 | 6 | 41677267 | 41677307 | 40 | TGGA | TFEB_intron |
| nc-MRPL2 | 6 | 43021976 | 43021988 | 12 | G | MRPL2_UTR |
| XPO5 | 6 | 43491676 | 43491683 | 7 | T | XPO5_exon |
| nc-B3GAT2 | 6 | 71578422 | 71578430 | 8 | C | B3GAT2_intron |
| TTK | 6 | 80751896 | 80751916 | 20 | A | TTK_exon |
| SEC63 | 6 | 108214754 | 108214764 | 10 | T | SEC63_exon |
| D6S474 | 6 | 112879151 | 112879231 | 80 | TAGA | intergenic |
| nc-TIAM2 | 6 | 155174524 | 155174535 | 11 | T | TIAM2_UTR |
| nc-EGFR | 7 | 55273591 | 55273604 | 13 | A | EGFR_UTR |
| TMEM60 | 7 | 77423459 | 77423468 | 9 | T | TMEM60_exon |
| D7S820 | 7 | 83789541 | 83789593 | 52 | TATC | SEMA3A_intron |
| TRRAP_1 | 7 | 98515231 | 98515239 | 8 | TG | TRRAP_exon |
| TRRAP_2 | 7 | 98535308 | 98535316 | 8 | CA | TRRAP_exon |
| TRRAP_3 | 7 | 98609744 | 98609751 | 7 | A | TRRAP_exon |
| SRRT | 7 | 100479331 | 100479339 | 8 | G | SRRT_exon |
| PIK3CG | 7 | 106526646 | 106526654 | 8 | AG | PIK3CG_exon |
| NOS3 | 7 | 150698397 | 150698404 | 7 | G | NOS3_exon |
| MLL3 | 7 | 151874147 | 151874156 | 9 | T | KMT2C_exon |
| WRN_1 | 8 | 30915970 | 30915978 | 8 | A | WRN_exon |
| WRN_2 | 8 | 31001131 | 31001138 | 7 | A | WRN_exon |
| D8S1115 | 8 | 42536588 | 42536615 | 27 | AAT | intergenic |
| nc-DEPDC2 | 8 | 68926682 | 68926690 | 8 | G | PREX2_intron |
| D8S1179 | 8 | 125907104 | 125907159 | 55 | TATC | intergenic |
| MYC | 8 | 128748844 | 128748851 | 7 | T | MYC_exon |
| nc-MYC | 8 | 128753393 | 128753403 | 10 | T | MYC_UTR |
| D9S1122 | 9 | 79688733 | 79688791 | 58 | TAGA | intergenic |
| PTCH1_1 | 9 | 98209616 | 98209623 | 7 | G | PTCH1_exon |
| PTCH1_2 | 9 | 98231380 | 98231388 | 8 | GT | PTCH1_exon |
| PTCH1_3 | 9 | 98268792 | 98268799 | 7 | T | PTCH1_exon |
| PTCH1_4 | 9 | 98270529 | 98270536 | 7 | C | PTCH1_exon |
| NOTCH1_1 | 9 | 139410440 | 139410448 | 8 | CA | NOTCH1_exon |
| NOTCH1_2 | 9 | 139413170 | 139413178 | 8 | AC | NOTCH1_exon |
| D10S1435 | 10 | 2243331 | 2243392 | 61 | TATC | intergenic |
| RET | 10 | 43600516 | 43600524 | 8 | GC | RET_exon |
| TFAM | 10 | 60148569 | 60148579 | 10 | A | TFAM_exon |
| PTEN | 10 | 89717718 | 89717726 | 8 | TG | PTEN_exon |
| FAS | 10 | 90768707 | 90768714 | 7 | T | FAS_exon |
| HPS1 | 10 | 100186986 | 100186994 | 8 | G | HPS1_exon |
| FGFR2 | 10 | 123278264 | 123278272 | 8 | AT | FGFR2_exon |
| D10S1248 | 10 | 131092507 | 131092559 | 52 | GGAA | intergenic |
| THO1 | 11 | 2192318 | 2192346 | 28 | ATGA | TH_intron |
| OR51E2 | 11 | 4703474 | 4703482 | 8 | A | OR51E2_exon |
| nc-SPON1 | 11 | 14162567 | 14162575 | 8 | C | SPON1_UTR |
| SLC22A9 | 11 | 63149670 | 63149681 | 11 | A | SLC22A9_exon |
| POLD3 | 11 | 74336608 | 74336617 | 9 | A | POLD3_exon |
| UVRAG | 11 | 75694430 | 75694440 | 10 | A | UVRAG_exon |
| NDUFC2 | 11 | 77784146 | 77784155 | 9 | A | NDUFC2_exon |
| nc-BIRC3 | 11 | 102193508 | 102193534 | 26 | A | BIRC3_UTR |
| CASP5_1 | 11 | 104878040 | 104878050 | 10 | T | CASP5_exon |
| CASP5_2 | 11 | 104879686 | 104879696 | 10 | T | CASP5_exon |
| ATM_1 | 11 | 108114816 | 108114823 | 7 | T | ATM_exon |
| ATM_2 | 11 | 108143279 | 108143287 | 8 | AT | ATM_exon |
| ATM_3 | 11 | 108216476 | 108216483 | 7 | A | ATM_exon |
| CHEK1 | 11 | 125505377 | 125505386 | 9 | A | CHEK1_exon |
| D11S4463 | 11 | 130872403 | 130872462 | 59 | TCTA | intergenic |
| WNK1 | 12 | 970296 | 970306 | 10 | A | WNK1_exon |
| vWA | 12 | 6093134 | 6093210 | 76 | TAGA | VWF_intron |

TABLE 2-continued

| STR ID | Chr | Start (0-base) | End (1-base) | hg19 length | Motif | Gene location |
|---|---|---|---|---|---|---|
| D12S391 | 12 | 12449953 | 12450029 | 76 | AGAT | intergenic |
| ERBB3 | 12 | 56492329 | 56492337 | 8 | AC | ERBB3_exon |
| MYO1A | 12 | 57422572 | 57422580 | 8 | T | MYO1A_exon |
| nc-AVIL | 12 | 58202496 | 58202506 | 10 | A | AVIL_intron |
| MDM2 | 12 | 69233089 | 69233096 | 7 | C | MDM2_exon |
| nc-SH2B3 | 12 | 111887735 | 111887749 | 14 | T | SH2B3_UTR |
| WASF3 | 13 | 27255386 | 27255394 | 8 | C | WASF3_exon |
| FLT3 | 13 | 28611378 | 28611386 | 8 | AT | FLT3_exon |
| RXFP2 | 13 | 32376428 | 32376438 | 10 | A | RXFP2_exon |
| BRCA2_1 | 13 | 32906602 | 32906609 | 7 | A | BRCA2_exon |
| BRCA2_2 | 13 | 32907420 | 32907428 | 8 | A | BRCA2_exon |
| BRCA2_3 | 13 | 32911073 | 32911080 | 7 | A | BRCA2_exon |
| BRCA2_4 | 13 | 32911442 | 32911449 | 7 | A | BRCA2_exon |
| BRCA2_5 | 13 | 32912345 | 32912352 | 7 | A | BRCA2_exon |
| BRCA2_6 | 13 | 32913558 | 32913565 | 7 | A | BRCA2_exon |
| BRCA2_7 | 13 | 32913836 | 32913843 | 7 | A | BRCA2_exon |
| BRCA2_8 | 13 | 32914953 | 32914961 | 8 | TC | BRCA2_exon |
| BRCA2_9 | 13 | 32953632 | 32953639 | 7 | A | BRCA2_exon |
| BRCA2_10 | 13 | 32954022 | 32954030 | 8 | A | BRCA2_exon |
| BRCA2_11 | 13 | 32954272 | 32954279 | 7 | A | BRCA2_exon |
| RFC3 | 13 | 34398062 | 34398072 | 10 | A | RFC3_exon |
| RB1 | 13 | 48881488 | 48881498 | 10 | AG | RB1_exon |
| RNASEH2B | 13 | 51530586 | 51530596 | 10 | A | RNASEH2B_exon |
| ERCC5 | 13 | 103524567 | 103524574 | 7 | A | ERCC5_exon |
| nc-IRS2 | 13 | 110407561 | 110407588 | 27 | T | IRS2_UTR |
| NR-21 | 14 | 23652346 | 23652367 | 21 | A | SLC7A8_exon |
| MLH3 | 14 | 75514603 | 75514612 | 9 | T | MLH3_exon |
| D14S1434 | 14 | 95308390 | 95308442 | 52 | CTAT | intergenic |
| HSP90AA1 | 14 | 102549429 | 102549436 | 7 | T | HSP90AA1_exon |
| NTRK3 | 15 | 88524505 | 88524513 | 8 | AT | NTRK3_exon |
| BLM_1 | 15 | 91304138 | 91304147 | 9 | A | BLM_exon |
| BLM_2 | 15 | 91310207 | 91310214 | 7 | A | BLM_exon |
| CHD2_1 | 15 | 93480818 | 93480826 | 8 | A | CHD2_exon |
| CHD2_2 | 15 | 93486250 | 93486257 | 7 | A | CHD2_exon |
| CHD2_3 | 15 | 93540315 | 93540325 | 10 | A | CHD2_exon |
| CHD2_4 | 15 | 93545433 | 93545442 | 9 | A | CHD2_exon |
| nc-LOC154820 | 15 | 96038161 | 96038170 | 9 | A | LOC154820_intron |
| TSC2_1 | 16 | 2114386 | 2114394 | 8 | CA | TSC2_exon |
| TSC2_2 | 16 | 2121790 | 2121798 | 8 | AG | TSC2_exon |
| CREBBP_1 | 16 | 3779210 | 3779217 | 7 | G | CREBBP_exon |
| CREBBP_2 | 16 | 3817720 | 3817727 | 7 | T | CREBBP_exon |
| GLYR1 | 16 | 4862228 | 4862236 | 8 | C | GLYR1_exon |
| MYH11 | 16 | 15802686 | 15802694 | 8 | G | NDE1_exon |
| nc-FTO | 16 | 54147723 | 54147738 | 15 | T | FTO_UTR |
| CDH1 | 16 | 68849487 | 68849495 | 8 | TC | CDH1_exon |
| D16S539 | 16 | 86386307 | 86386351 | 44 | GATA | intergenic |
| NF1_1 | 17 | 29486049 | 29486070 | 21 | TC | NF1_exon |
| NF1_2 | 17 | 29553477 | 29553484 | 7 | C | NF1_exon |
| NF1_3 | 17 | 29579995 | 29580002 | 7 | A | NF1_exon |
| NF1_4 | 17 | 29664534 | 29664544 | 10 | GA | NF1_exon |
| D17S250 | 17 | 37152123 | 37152163 | 40 | GT | intergenic |
| nc-STAT3 | 17 | 40532591 | 40532599 | 8 | G | STAT3_UTR |
| BRCA1_1 | 17 | 41215950 | 41215958 | 8 | CA | BRCA1_exon |
| BRCA1_2 | 17 | 41245586 | 41245594 | 8 | T | BRCA1_exon |
| BRCA1_3 | 17 | 41246531 | 41246538 | 7 | T | BRCA1_exon |
| COL1A1 | 17 | 48266554 | 48266562 | 8 | CT | COL1A1_exon |
| XYLT2 | 17 | 48433966 | 48433973 | 7 | C | XYLT2_exon |
| D17S1301 | 17 | 72680993 | 72681041 | 48 | AGAT | RAB37_intron |
| nc-TNRC6C | 17 | 76101834 | 76101843 | 9 | T | TNRC6C_UTR |
| LMAN1 | 18 | 57013193 | 57013202 | 9 | T | LMAN1_exon |
| D18S51 | 18 | 60948899 | 60948971 | 72 | AGAA | BCL2_intron |
| DNMT1_1 | 19 | 10262138 | 10262145 | 7 | T | DNMT1_exon |
| DNMT1_2 | 19 | 10270725 | 10270732 | 7 | T | DNMT1_exon |
| DNMT1_3 | 19 | 10291083 | 10291090 | 7 | G | DNMT1_exon |
| nc-ELAVL3 | 19 | 11564007 | 11564018 | 11 | G | ELAVL3_UTR |
| ELAVL3 | 19 | 11577604 | 11577613 | 9 | C | ELAVL3_exon |
| OR7C1 | 19 | 14910637 | 14910647 | 10 | A | OR7C1_exon |
| D19S433 | 19 | 30417140 | 30417206 | 66 | TCCT | URI1_intron |
| nc-ZNF302 | 19 | 35175076 | 35175125 | 49 | A | ZNF302_intron |
| nc-FBXO46 | 19 | 46214700 | 46214714 | 14 | A | FBXO46_UTR |
| BAX | 19 | 49458970 | 49458978 | 8 | G | BAX_exon |
| TEAD2 | 19 | 49850472 | 49850480 | 8 | C | TEAD2_exon |
| FLT3LG | 19 | 49982165 | 49982174 | 9 | C | FLT3LG_exon |
| D20S482 | 20 | 4506337 | 4506393 | 56 | AGAT | intergenic |
| SLC23A2 | 20 | 4850568 | 4850577 | 9 | G | SLC23A2_exon |
| nc-SEMG1 | 20 | 43837375 | 43837384 | 9 | T | SEMG1_UTR |
| ZMYND8 | 20 | 45875071 | 45875079 | 8 | T | ZMYND8_exon |

TABLE 2-continued

| STR ID | Chr | Start (0-base) | End (1-base) | hg19 length | Motif | Gene location |
|---|---|---|---|---|---|---|
| D20S1082 | 20 | 53865937 | 53865979 | 42 | ATA | intergenic |
| D21S11 | 21 | 20554291 | 20554409 | 118 | TCTA | intergenic |
| GART | 21 | 34882121 | 34882131 | 10 | T | GART_exon |
| D22S1045 | 22 | 37536326 | 37536382 | 56 | ATT | IL2RB_intron |
| EP300_1 | 22 | 41566524 | 41566531 | 7 | A | EP300_exon |
| EP300_2 | 22 | 41574618 | 41574626 | 8 | TC | EP300_exon |
| nc-ARHGAP8 | 22 | 45205158 | 45205169 | 11 | T | ARHGAP8_intron |
| nc-SLC9A7 | X | 46505053 | 46505072 | 19 | T | SLC9A7_intron |
| AR | X | 66931483 | 66931491 | 8 | GA | AR_exon |
| nc-AMOT | X | 112023977 | 112023986 | 9 | A | AMOT_intron |
| DYS19 | Y | 9521988 | 9522036 | 48 | TCTA | intergenic |
| DYS391 | Y | 14102794 | 14102838 | 44 | TCTA | intergenic |
| DYS437 | Y | 14466993 | 14467057 | 64 | TCTA | intergenic |
| DYS388 | Y | 14747534 | 14747570 | 36 | AAT | intergenic |
| Y-GATA-H4 | Y | 18743514 | 18743600 | 86 | TCTA | intergenic |
| DYS460 | Y | 21050841 | 21050881 | 40 | CTAT | intergenic |
| DYS392 | Y | 22633875 | 22633911 | 36 | ATA | TTTY10_intron |

TABLE 3

| gene | chr | start | end | Target | Role in DNA repair and genome stability |
|---|---|---|---|---|---|
| MTOR | 1 | 11167541 | 11319466 | All exons | NA |
| ARID1A | 1 | 27022894 | 27107247 | All exons | NA |
| JAK1 | 1 | 65300244 | 65351947 | All exons | NA |
| NRAS | 1 | 1.15E+08 | 1.15E+08 | All exons | NA |
| FLG | 1 | 1.52E+08 | 1.52E+08 | All exons | NA |
| KIAA1804 | 1 | 2.33E+08 | 2.34E+08 | All exons | NA |
| MSH2 | 2 | 47630330 | 47710088 | All exons | DNA repair, mismatch repair, maintenance of DNA repeat elements, DNA integrity checkpoint, DNA recombination |
| MSH6 | 2 | 48010372 | 48033999 | All exons | DNA repair, mismatch repair, DNA recombination |
| TET3 | 2 | 74273449 | 74329303 | All exons | NA |
| ACVR2A | 2 | 1.49E+08 | 1.49E+08 | All exons | NA |
| STAT1 | 2 | 1.92E+08 | 1.92E+08 | All exons | NA |
| ERBB4 | 2 | 2.12E+08 | 2.13E+08 | All exons | NA |
| VHL | 3 | 10183531 | 10191649 | All exons | NA |
| RAF1 | 3 | 12626012 | 12660220 | All exons | NA |
| TGFBR2 | 3 | 30648375 | 30733091 | All exons | NA |
| MLH1 | 3 | 37035038 | 37092144 | All exons | DNA repair, mismatch repair, DNA recombination |
| CTNNB1 | 3 | 41265559 | 41280833 | All exons | NA |
| PIK3CA | 3 | 1.79E+08 | 1.79E+08 | All exons | NA |
| FGFR3 | 4 | 1795661 | 1808989 | All exons | NA |
| PDGFRA | 4 | 55124935 | 55161439 | All exons | NA |
| KIT | 4 | 55524181 | 55604723 | All exons | NA |
| TET2 | 4 | 1.06E+08 | 1.06E+08 | All exons | NA |
| PCDH10 | 4 | 1.34E+08 | 1.34E+08 | All exons | NA |
| FBXW7 | 4 | 1.53E+08 | 1.53E+08 | All exons | NA |
| MAP3K1 | 5 | 56111400 | 56189507 | All exons | NA |
| MSH3 | 5 | 79950546 | 80171681 | All exons | DNA repair, mismatch repair, maintenance of DNA repeat elements, DNA recombination |
| APC | 5 | 1.12E+08 | 1.12E+08 | All exons | NA |
| CSF1R | 5 | 1.49E+08 | 1.49E+08 | All exons | NA |
| VEGFA | 6 | 43738443 | 43752365 | All exons | NA |
| ESR1 | 6 | 1.52E+08 | 1.52E+08 | All exons | NA |
| PMS2 | 7 | 6013029 | 6048650 | All exons | mismatch repair |
| GLI3 | 7 | 42003927 | 42262852 | All exons | NA |
| EGFR | 7 | 55086970 | 55273310 | All exons | NA |
| TRRAP | 7 | 98478773 | 98609978 | All exons | DNA repair |
| MET | 7 | 1.16E+08 | 1.16E+08 | All exons | NA |
| BRAF | 7 | 1.4E+08 | 1.41E+08 | All exons | NA |
| WRN | 8 | 30915963 | 31030618 | All exons | DNA repair, DNA recombination |
| FGFR1 | 8 | 38271145 | 38318624 | All exons | NA |
| TRPS1 | 8 | 1.16E+08 | 1.17E+08 | All exons | NA |
| MYC | 8 | 1.29E+08 | 1.29E+08 | All exons | NA |
| JAK2 | 9 | 5021987 | 5126791 | All exons | NA |

TABLE 3-continued

| gene | chr | start | end | Target | Role in DNA repair and genome stability |
|---|---|---|---|---|---|
| CDKN2A | 9 | 21968227 | 21994330 | All exons | NA |
| ABL1 | 9 | 1.34E+08 | 1.34E+08 | All exons | DNA repair, mismatch repair |
| RET | 10 | 43572706 | 43623717 | All exons | NA |
| MAPK8 | 10 | 49609703 | 49643072 | All exons | NA |
| PTEN | 10 | 89624226 | 89725229 | All exons | NA |
| TCF7L2 | 10 | 1.15E+08 | 1.15E+08 | All exons | maintenance of DNA repeat elements |
| FGFR2 | 10 | 1.23E+08 | 1.23E+08 | All exons | NA |
| HRAS | 11 | 532635 | 534322 | All exons | NA |
| ATM | 11 | 1.08E+08 | 1.08E+08 | All exons | DNA repair, DNA integrity checkpoint, DNA recombination |
| KRAS | 12 | 25362728 | 25398318 | All exons | NA |
| ACVR1B | 12 | 52345527 | 52387894 | All exons | NA |
| ERBB3 | 12 | 56474084 | 56495839 | All exons | NA |
| CDK4 | 12 | 58142307 | 58145500 | All exons | NA |
| POLE | 12 | 1.33E+08 | 1.33E+08 | Exon 13 | DNA repair |
| FLT3 | 13 | 28578188 | 28674647 | All exons | NA |
| RB1 | 13 | 48878048 | 49054207 | All exons | NA |
| EDNRB | 13 | 78470576 | 78493750 | All exons | NA |
| GPC6 | 13 | 93879709 | 95055471 | All exons | NA |
| TEP1 | 14 | 20836595 | 20876598 | All exons | DNA recombination |
| MARK3 | 14 | 1.04E+08 | 1.04E+08 | All exons | NA |
| AKT1 | 14 | 1.05E+08 | 1.05E+08 | All exons | NA |
| MAP2K1 | 15 | 66679685 | 66782953 | All exons | NA |
| MAPK3 | 16 | 30127988 | 30134530 | All exons | NA |
| TP53 | 17 | 7572926 | 7579912 | All exons | DNA repair, DNA integrity checkpoint |
| ERBB2 | 17 | 37856491 | 37884297 | All exons | NA |
| STAT3 | 17 | 40467762 | 40500534 | All exons | NA |
| AXIN2 | 17 | 63526093 | 63554738 | All exons | maintenance of DNA repeat elements |
| PRKCA | 17 | 64298969 | 64800155 | All exons | NA |
| SOX9 | 17 | 70117532 | 70120528 | All exons | NA |
| SMAD2 | 18 | 45368197 | 45423127 | All exons | NA |
| SMAD4 | 18 | 48573416 | 48604837 | All exons | NA |
| NARS | 18 | 55268883 | 55288949 | All exons | NA |
| STK11 | 19 | 1206912 | 1226646 | All exons | NA |
| MAP2K2 | 19 | 4090595 | 4123872 | All exons | NA |
| MAP2K7 | 19 | 7968829 | 7977316 | All exons | NA |
| AKT2 | 19 | 40739778 | 40771174 | All exons | NA |
| POLD1 | 19 | 50909663 | 50909774 | Exon 11 | DNA repair, mismatch repair |
| SRC | 20 | 36012556 | 36031782 | All exons | NA |
| PLCG1 | 20 | 39766281 | 39803149 | All exons | NA |
| AURKA | 20 | 54945213 | 54963253 | All exons | DNA integrity checkpoint |
| TPTE | 21 | 10906904 | 10973733 | All exons | NA |
| MAPK1 | 22 | 22123492 | 22221730 | All exons | NA |
| ARAF | X | 47422366 | 47430856 | All exons | NA |
| FAM123B | X | 63409758 | 63413166 | All exons | NA |

Microsatellite Mutation Calling

Figure 8:
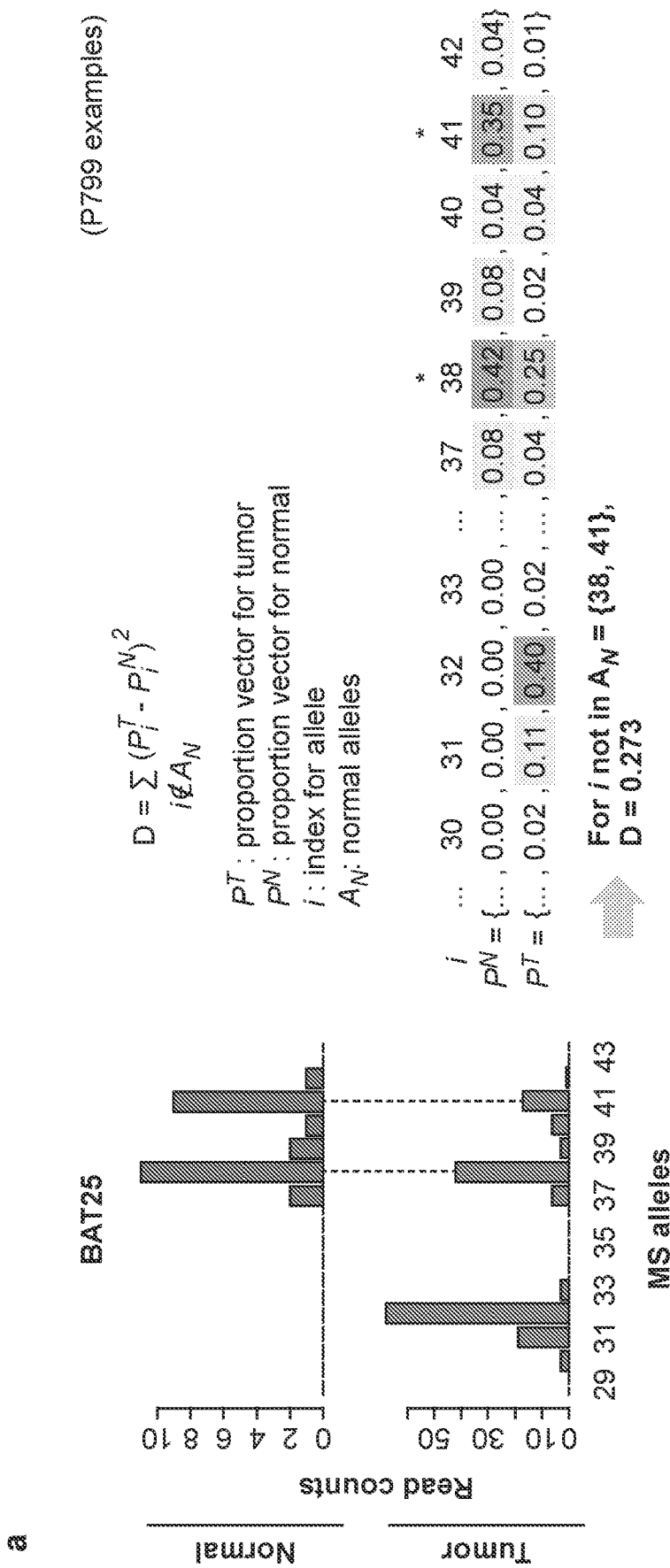
FIG. 8 provides determination of microsatellite allelic shift. (a) Definition of microsatellite distance between tumor and normal samples. An example of allelic shift at the BAT25 locus of the P799 tumor is shown. Left panels show the allele histograms generated by the OS-Seq method. Relative abundance (sequencing read count) of DNA molecules and different microsatellite alleles (number of motif repeats) are indicated on the y-and x-axes, respectively. From the normal allele profile, the heterozygote alleles (38 and 41 motif repeats) are apparent. The allele proportion is calculated by dividing the read count of each allele by the total read count from the locus. The example shown at the bottom right are the proportion vectors from the normal and tumor samples ($P^N$ and $P^T$), and the distance value calculated following the definition of microsatellite distance provided at the top right. (b) Kernel density distribution of microsatellite distance values from all 46 tumor/normal comparisons at 225 microsatellite loci. The distribution is separately shown for mono-/dinucleotide and tri-/tetranucleotide microsatellites. Mixture of two Gaussian distributions are assumed: one for wild type, and the other for shifted alleles. A threshold (dotted vertical line) is indicated at the intersection of the two density curves.
Figure 8:
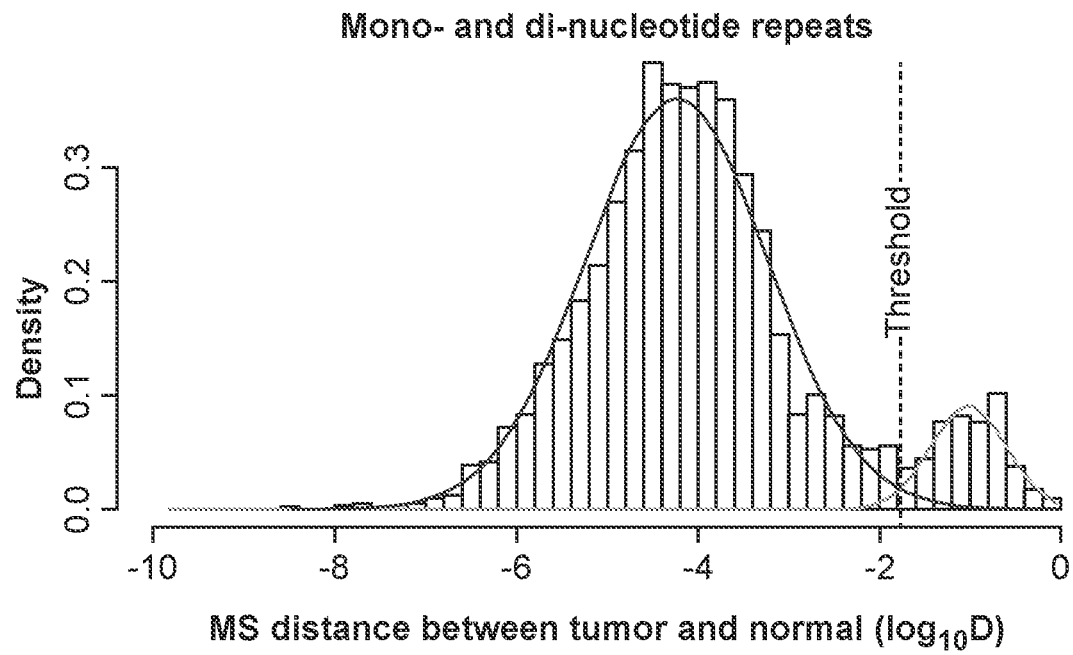
Figure 8:
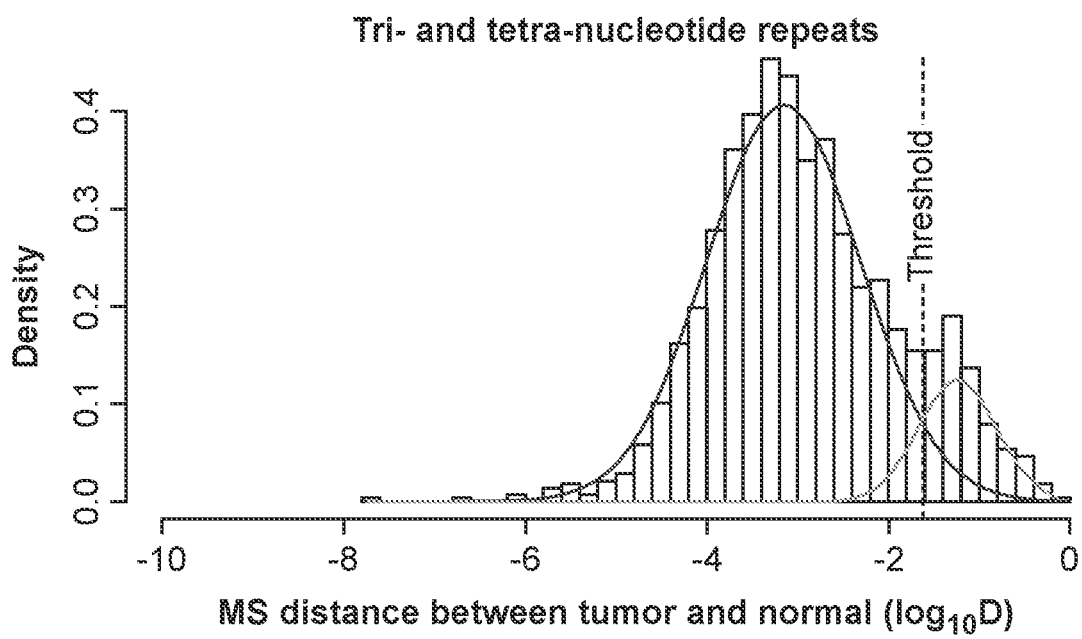

A bioinformatics pipeline was developed to identify somatic changes to microsatellites [23]. An overview of the microsatellite genotyping process is illustrated in FIG. 1a. Briefly, after single-end alignment to the NCBI v37 genome, a custom SAM file tag (ZP) was added to the aligned reads. This tag denotes which microsatellite probe generated the read as well as the linked target STR information (e.g. repeat motif and flanking sequences). The Read 2 (R2) aligned sequences, which include the capture probe sequence and residual genomic sequences, were used to determine the tag for paired end reads. This indexing method does not require Read 1 (R1) sequences to align to the genome; both aligned and unaligned reads are tagged based on alignment of their R2 mate to a designated primer probe sequence. After the indexing, reads are evaluated to determine whether both the expected 5' and 3' STR flanking sequences are present in R1. For this study, the 'STR-spanning' reads, which contain a combined sequence that includes an 8 base 5' flanking sequence, a variable length region containing at least a minimum number of STR motif repeats, and an 8 base 3' flanking region, were aggregated. Using the reads that contain this combined sequence, the STR motif repeat count was calculated by dividing the number of bases in the variable length region by the length of the STR motif. For example, if the variable length region is 28 bases and the STR motif is GATA (tetranucleotide), then the STR motif repeat count is seven. The R1 reads encompassing entire STRs (i.e. STR-spanning reads) are counted and summarized by motif repeat count (i.e. allele) to provide a basis for determining the genotype and extent of mutations in microsatellites (MS). The distribution of alleles and relative percentage of reads for each allele was used to compare tumor versus normal samples (FIG. 8 a).

For a given MS locus, $y=(y_1, \ldots, y_n)$ is the read count for each of the n alleles. Letting $S=\Sigma_i y_i$ be the total number of reads observed for the locus, the allele coverage proportion vector for the MS was computed as follows:

$$p = (p_1, \ldots, p_n), \ p_i = \frac{y_i}{S}.$$

These proportion vectors exhibited peaks at alleles that are present in a sample. Using samples from a matched normal source, alleles $A_N$ were first determined based on the criteria previously described [23]. $n(A_N) \leq 2$ was assumed. To determine whether a MS locus has a somatic allele shift in tumor DNA T versus its paired normal N, a weighted Euclidean distance between the two proportion vectors was used:

$$D = \sum_{i \notin A_N} (p_i^T - p_i^N)^2.$$

The proportions of normal alleles, $A_N$, were excluded when calculating D (i.e. a zero weight for normal alleles). This weighting minimized the contribution of copy number changes in the distance. If D is greater than a given threshold, it is considered that the MS locus has an allele shift. The threshold was decided to minimize false positive and negative rates after fitting a most probable Gaussian mixture densities to the data (FIG. 8b). To evaluate the extent of MSI of a tumor, the fraction of MS loci with allele shift versus the total number of measured MS loci was calculated.

Microsatellite PCR Genotyping

For mononucleotide repeat instability, the PowerPlex MSI analysis system v1.2 (Promega) was used to test five markers following the manufacturer's protocol. For EMAST, a set of primers that amplify tetranucleotide microsatellites (D20S82, D20S85, D8S321, D9S242, and MYCL1) as has been previously published was used [12]. The 12.5-µl reaction included two ng of gDNA, 0.4 µM each primer, 1× Buffer I with $MgCl_2$, 0.2 mM each dNTP, and 1.25 units of AmpliTaq Gold polymerase (Thermo Fisher Scientific, Waltham, MA). The samples were denatured at 95° C. for 5 min, followed by 35 cycles of 30 sec at 95° C., 90 sec at 58° C., and 30 sec at 72° C. The final steps for amplification involved an incubation at 72° C. for 10 min and cooling to 4° C. ABI 3130x1 Genetic Analyzer (Thermo Fisher Scientific) was used with a recommended matrix standard setting. PowerPlex 4C (Promega) and DS-33 (Thermo Fisher Scientific) matrix standard kits were used for the mono- and tetranucleotide repeat assays, respectively. Using the raw signal data (fsa files), Peak Scanner v1.0 (Thermo Fisher Scientific) program provided the size of detected amplicons. A criterion where a shift in allele size of 3 bp or more in the tumor samples compared to matching normal sample indicated instability at a given MS locus was used.

Identifying Copy Number Alterations

The data from paired-end alignment was used to determine copy number analysis and somatic mutation calling. As with MSI analysis, the 'ZP' sam tag is added to both R1 and R2 reads. The number of reads sharing each primer ID is found by counting 'ZP' tags and represents how many DNA molecules are captured by the primer. Therefore, by comparing the per-probe read counts between tumor and normal samples, copy number changes can be measured. The per-probe read counts were first normalized by the total number of reads from all the probes, and then the log 2 ratio between tumor versus normal was calculated. When calculating the ratio, the probes that showed high variation from normal DNA as determined by a Z-score were excluded. Specifically, the probes having a Z-score greater than 2 or less than −2 were excluded. In addition, systemic biases of the log 2 ratios were corrected in terms of GC % of probe capture sequence and the per-probe read counts. The adjustments were made by the locally weighted scatterplot smoothing (LOWESS) method. For example, the values at the regression line were set to zero. Using the per-probe ratio, which were normalized and corrected, median ratios for all the target genes were calculated as a representation of copy number. These values were used for generating heat maps as well. The per-gene median ratios were also used in comparison with whole genome sequencing ratios.

Copy Number Classification

An extreme gradient boosting algorithm called XGBoost was used to train a multi-class model and make predictions about the copy number classification [25]. The XGBoost method was implemented in the R package xgboost. The copy number data from the CRC TCGA study was used as the training set. For all analysis, the softprob objective function was used and it was run 100 times. Other training parameters such as eta, gamma, minimum child weight and maximum depth were all set as default values. An XGBoost model was then trained on the copy number cluster labels, using the 82 signature genes as features from the targeted sequencing assay.

Identifying Gene Mutations

Paired-end alignment was used for detection of somatic mutation. The Sentieon TNseq package (v201808.03; Sentieon Inc, Mountain View, CA) was used to preprocess the alignments and to call somatic variants following the best practice guideline. Sentieon TNseq consists of tools that are based on Mutect and Mutect2 [26]. In the mutation calling analysis, duplicates were not marked because the OS-Seq libraries are prepared without PCR amplification, i.e. a single read represents a single molecule. In addition, the first 40 bases of R2 reads were masked as N bases because they did not originate from the sample's gDNA, but from the OS-Seq probes. Mutations were considered pathogenic if they had a CADD score greater than 20 [27].

Whole Genome Sequencing

To assess the accuracy of copy number analysis, matching tumor and normal samples from four patients were sequenced using the Illumina MiSeq or NextSeq platform (Illumina, San Diego, CA, USA). Sequencing libraries were prepared using 50 ng of DNA with the Illumina Nextera DNA Sample Prep Kit as per the manufacturer's protocol (ver. October 2012). The libraries were sequenced with a paired-end read length of 150 bp. The sequence data was automatically index-assigned (i.e. normal and tumor) and aligned with BWA [28], using default parameters, against human genome build 37. Duplicate reads were removed. The data was sorted and indexed with samtools [29]. The program CNVkit [30] was used to identify copy number alterations.

Linked read sequencing was used to retain long-range genomic information from three tumor/normal sample pairs. The sequencing library for the samples was prepared using the Chromium Library Kit (10× Genomics) following the manufacturer's protocol. The library was sequenced using the Illumina NovaSeq 6000 system with 150 by 150-bp paired-end reads. The resulting BCL files were converted to fastq files using Long Ranger (v2.1.2) 'mkfastq', then Long Ranger (v2.1.2) 'wgs' was run to align the reads to GRCh37.1 and detect rearrangements. Somatic variants were called using the Sentieon TNseq package (v201808.03) and copy number alteration using CNVkit [30] was determined following the best practice guidelines.

Digital PCR Validation of Specific Copy Number Alterations

The digital PCR assays were run on a QX200 droplet digital PCR system (Bio-Rad) per the manufacturer's guidelines. Each patient sample was assessed with three independent replicates for gene copy number. For samples analyzed in the hydrolysis probe-based assay, droplets were clustered using QuantaSoft (version1.2.10.0).

Identification of Chromosome Arm Alterations in TCGA CRC Samples

TCGA CRC copy number alterations were downloaded [31]. CNTools R package was then used to convert the segment data to gene level data. A log 2 ratio greater than 0.2 was considered as copy number gain, and less than −0.2 was considered as copy number loss. A chromosome arm-wide event was defined as copy number alterations among 50% or more of genes located in a given chromosome arm and having a consistent gain or loss. For samples labeled as MSS, MSI-low (MSI-L), or MSI-H, the frequency of arm-wide events was calculated by number of altered samples divided by the total number in each categories.

Results

Evaluating Diverse Microsatellite Classes and Cancer Drivers

A cancer sequencing approach was developed to identify somatic alterations for the major classes of tandem repeat motifs and to detect the presence of other genomic instability features, such as copy number alterations (FIG. 1 a). In addition to mutations and copy number, this method enables simultaneous characterization of multiple features of genomic instability such as MSI, EMAST, CIN and clonal architecture. The sequencing approach had a number of features that are significantly different than conventional targeted methods, such as bait hybridization capture or PCR amplicons [21, 22]. Specifically, this cancer sequencing technology uses multiplexed pools of primer probes that anneal to a genomic region-of-interest. One probe is used for a single target. After target-specific hybridization has occurred, the individual primer mediates a polymerase extension, replicating the downstream target DNA for sequencing (FIG. 9). Targeting can be massively multiplexed for tens of thousands of targets if not higher. This method has several advantages. First, sequencing a specific microsatellite requires only identifying a single primer with a length in the tens rather having to select two primers in PCR or using a bait hybridization oligonucleotide. This is an important feature as many important microsatellites are flanked by repetitive sequences which complicate targeting. Second, the primer used in targeting is sequenced in addition to the adjacent genome sequence and this information provides an index specific to the microsatellite. This feature is used to improve identification and subsequent microsatellite length calling. Third, the assay can be configured to target multiple tens of thousands of targets in a single multiplexed reaction, which enables us to ascertain the status of many microsatellite in parallel. Fourth, as is shown, the assessment of copy number changes is highly accurate. Finally, this approach enables us to eliminate one of the major steps in library amplification, reducing the extent of amplification errors. Given these advantages, microsatellite genotypes across different motifs were determined with high sensitivity and specificity, MSI was quantitated based on this expanded signature and provided highly accurate copy number levels. The accuracy of the copy number levels was confirmed by corroborating with digital PCR and whole genome sequencing.

To improve the detection of somatic alterations that occur at lower allelic fractions, exceptionally high sequencing coverage of microsatellite and gene targets was used, averaging 2,865× coverage per a sample. To reduce PCR artifacts, the sequencing library preparation was optimized by eliminating the PCR amplification steps (FIG. 9). As a result of this optimization, the number of PCR-related artifacts related to amplification stutter in repetitive sequences are reduced significantly as previously demonstrated [23]. As demonstrated previously, the elimination of PCR amplification means that each sequence read represents an individual DNA molecule [23]. Thus, there is no need for removing duplicate sequences arising from the amplification of the same molecule [23]. Removing PCR amplification improves the detection of i) microsatellite alleles which are present at low allelic fractions [23], and ii) microsatellite allele shifts which are less than 3 bp in size.

225 microsatellite markers and 1,387 exons from 85 cancer genes involved in CRC biology were examined (Table 1). The microsatellite markers included the following: 144 mononucleotides; 37 dinucleotides; 6 trinucleotides; 38 tetranucleotide motifs. Many of these markers had been previously used in other genotyping studies (Table 2). This diversity of microsatellites allowed us to distinguish different types of MSI including conventional MSI-high (MSI-H) and elevated microsatellite alterations at selected tetranucleotide repeats (EMAST). Among the microsatellite markers with mononucleotide repeats, their motif count (i.e. number of repeats) ranged from seven to 49. For the dinucleotide repeats, the motif count ranged from four up to 21. For the trinucleotide repeats, the motif count ranged from 9 to 18. For the tetranucleotide repeats, the motif count ranged from seven to 29. All five microsatellites that are part of the Bethesda criteria including those with mononucleotide repeats (BAT25, BAT26) and dinucleotide repeats were included (D2S123, D5S346, D17S250) [3].

Leveraging the results of the Cancer Genome Atlas Project (TCGA), 85 cancer genes that have among the highest frequency of mutations in CRC and are known cancer drivers were identified [1]. These 85 genes were located across all autosomal chromosomes, as well as the X chromosome, and included APC, TP53, KRAS and other well-established cancer genes [1, 32].

Analysis of Colorectal Cancer

Forty-six CRCs were used for this study. A subset of the samples had prior clinical testing for the presence of MSI. All of these samples had matched tumor and normal pairs. Somatic alterations in microsatellites, driver mutations and copy number alterations from 225 microsatellite markers and 1,387 exons from 85 cancer driver genes were identified.

Figure 10:
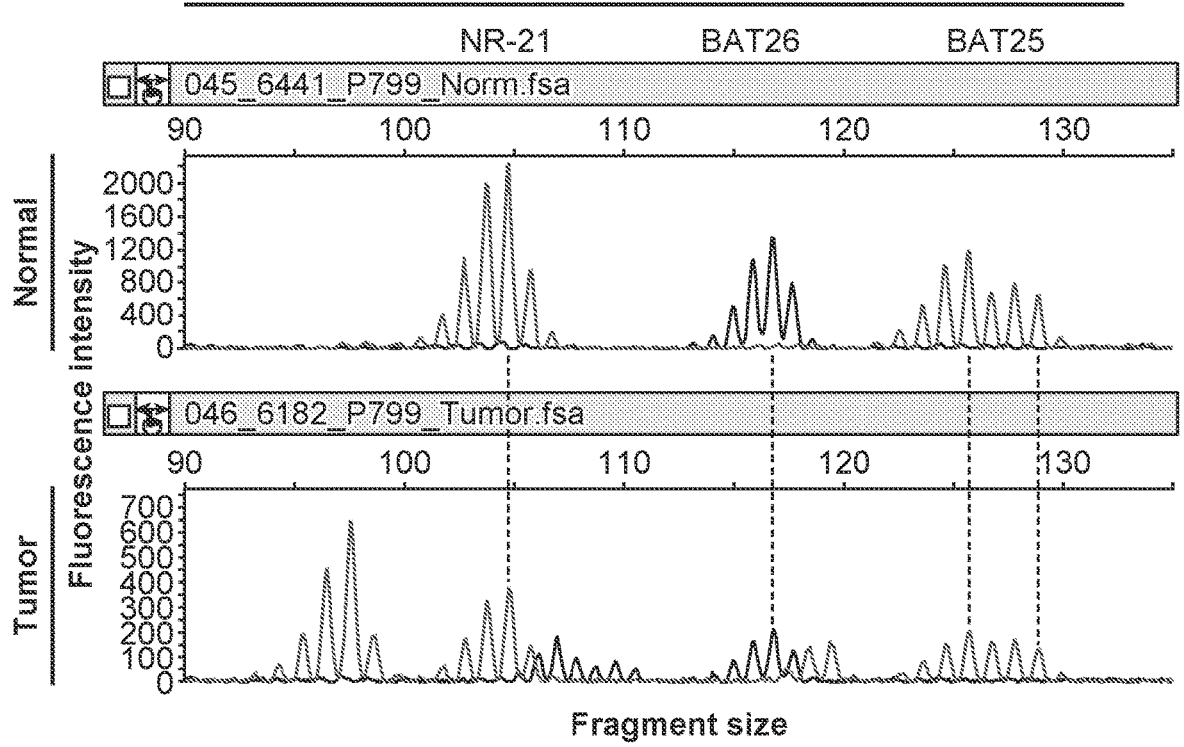
FIG. 10 a-b provides microsatellite allelic shifts detected by PCR-CE and OS-Seq methods. For three microsatellite loci (NR-21, BAT26, and BAT25), allele profiles of both normal and tumor samples are shown for two examples (P799 and P592 cases). The P799 and P592 tumors are classified as MSI and MSS according to the sequencing analysis. Electropherograms generated by PCR-CE method (top panels) provide relative abundance (y-axis, fluorescence intensity) of amplicons with different sizes (x-axis, DNA size in bp). Although it has erroneous stutter amplification, the tumor allele profile from the P799 tumor (MSI) suggests allele shifts. On the other hand, the tumor allele profile from the P592 tumor (MSS) shows no change compared to the normal profile. The allele histograms generated by the targeted sequencing analysis method (bottom panels) provide relative abundance (y-axis, sequencing read count) of DNA molecules, including different microsatellite alleles (x-axis, number of motif repeats). The microsatellite profiles show dramatically decrease stutter amplification compared to the profiles generated by PCR-CE method. For the P799 tumor, the PCR-CE and targeted sequencing profile match. However, for the P592 tumor, the sequencing profile show allele shifts at BAT26 and BAT25 loci (black arrows), which are invisible from the PCR-CE profile due to the stutter errors.
Figure 10:
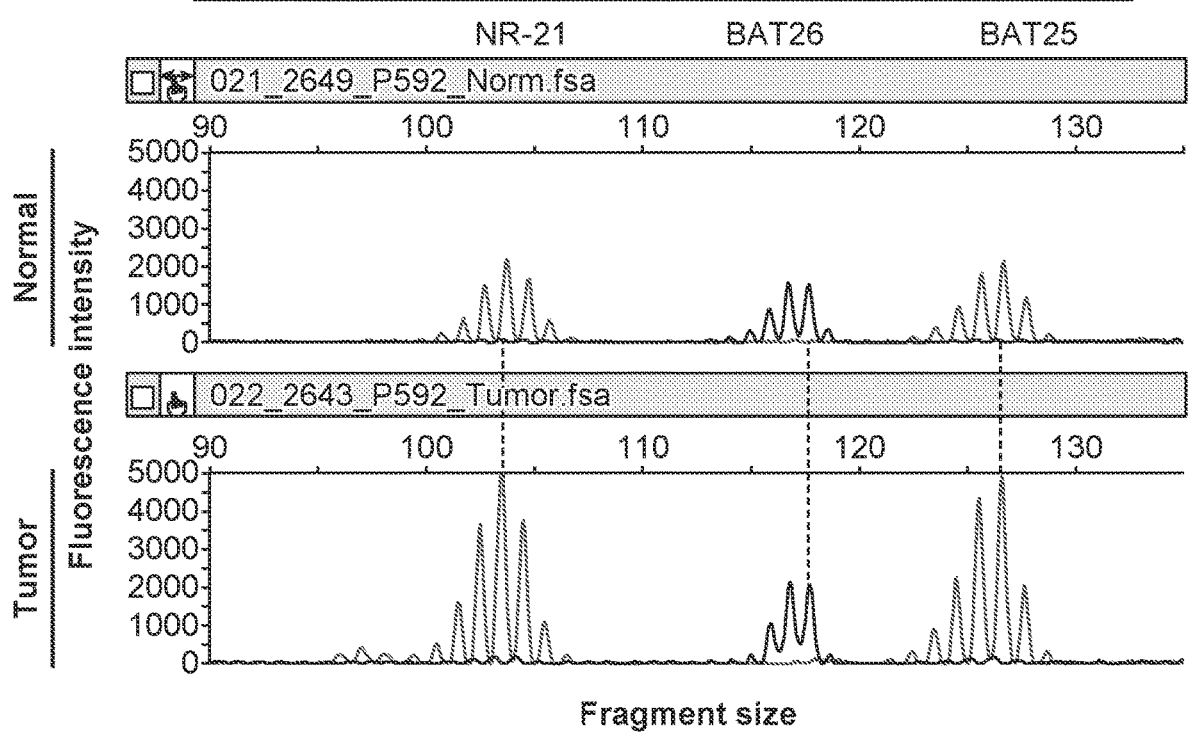
Figure 10:
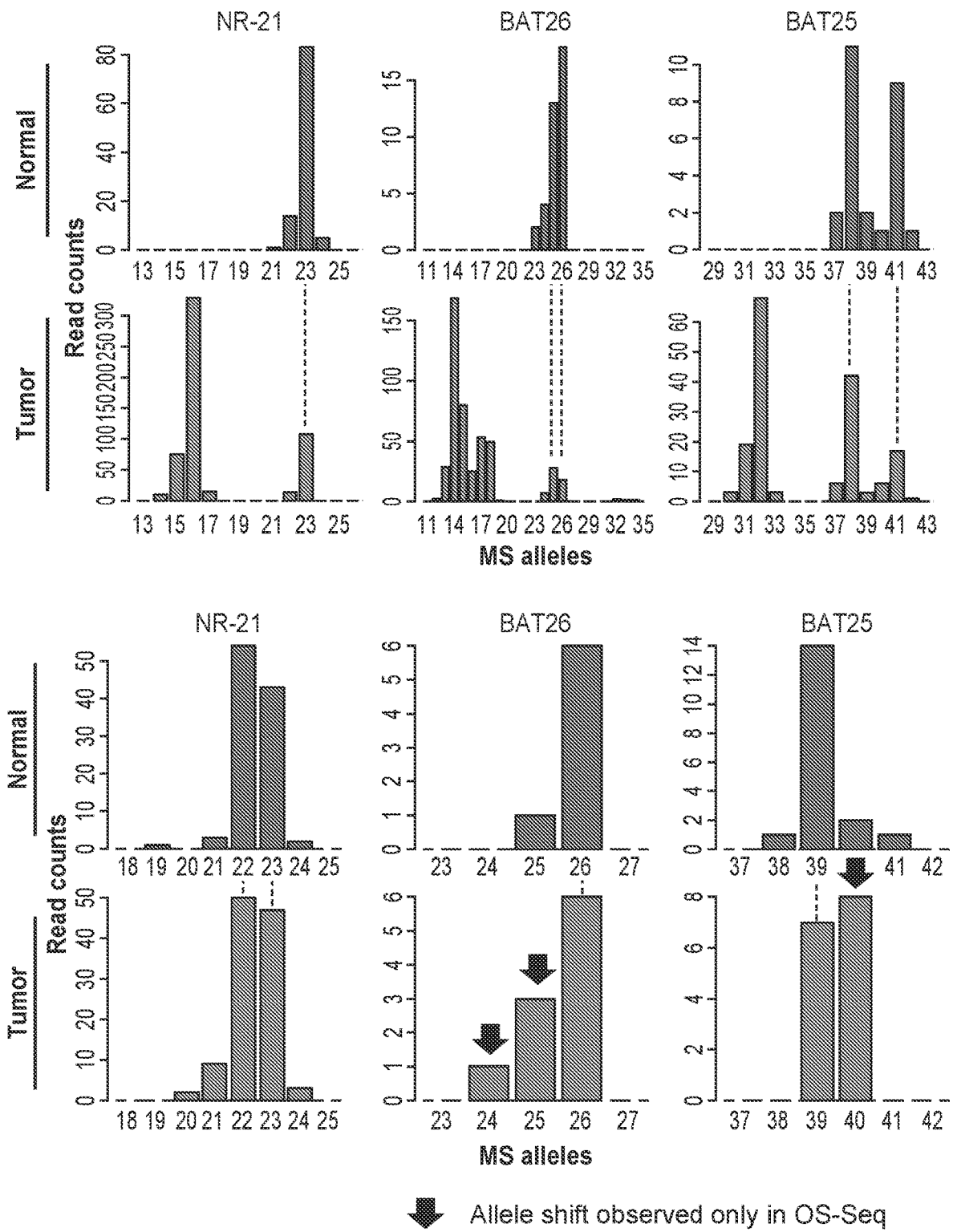

A new analytical method was developed for determining microsatellite mutations and MSI quantitation. For a given MS locus, the distance between two samples was calculated using all the observed MS alleles (Methods; FIG. 8 a); an allele coverage proportion vector for any given microsatellite was determined. This algorithm leveraged the improvements in sequencing data quality that resulted from reducing amplification stutter and eliminating artifactual microsatellite alleles (FIG. 10) [23].

Figure 2:
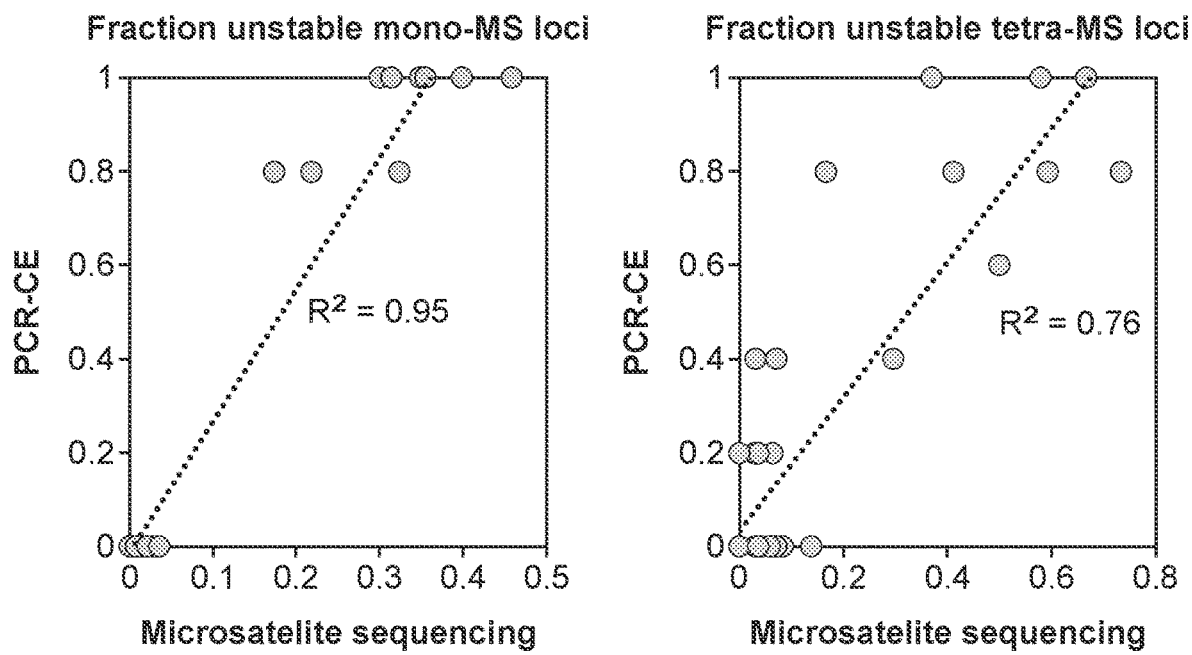
FIG. 2 a-c provides comparison with conventional methods. (a) Comparison with PCR genotyping for mono-or tetranucleotide repeat microsatellites. For each of 46 CRCs, the fraction of unstable loci was calculated in each microsatellite class by dividing the number of somatic allele shift mutations by the total number of genotyped microsatellites. For PCR genotyping assays, five microsatellite markers were used for each. For the sequencing assay, 144 mono-and 38 tetranucleotide repeat microsatellites were used, respectively. (b) and (c) Comparison with digital PCR (dPCR) and whole genome sequencing (WGS) for gene copy numbers. For each of 46 CRCs, the log 2 gene copy number ratio between tumor versus matched normal samples was calculated as described in Methods. To validate the NGS results, seven genes (VEGFA, MET, FGFR1, CDK4, FLT3, ERBB2, and AURKA) were selected for dPCR testing. For comparison with WGS, 83 target genes were used. In all the plots, dotted black lines indicate linear regression, and the correlation is indicated as an R-squared value.
Figure 2:
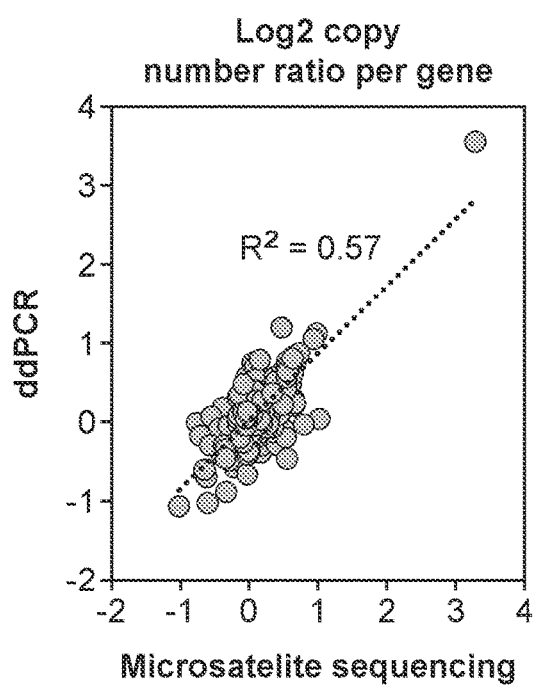
Figure 2:
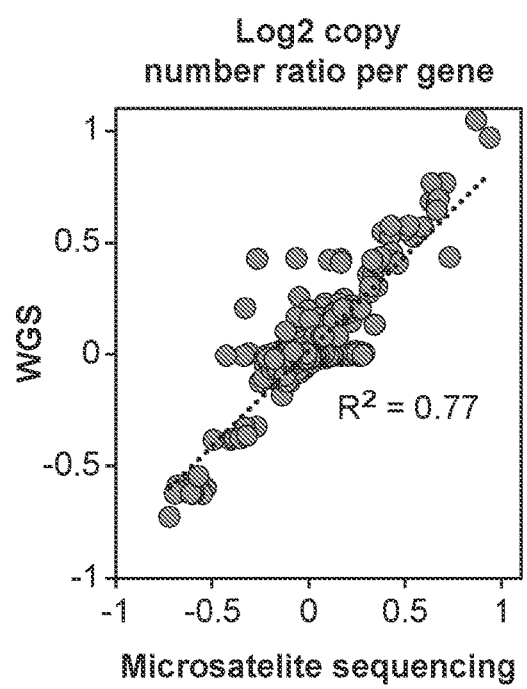

Next, the sequencing-based microsatellite genotypes were compared to the results from two PCR assays with different microsatellite panels and measured via capillary electrophoresis. The first PCR assay tested microsatellites with mononucleotide repeats. The second assay tested those with tetranucleotide repeats that have been used to characterize EMAST. All of the samples were genotyped with both PCR assays. Overall, there was a high correlation between the targeted sequencing and PCR-based genotypes ($R^2=0.95$ for mononucleotide repeats, $R^2=0.76$ for tetranucleotide repeats; FIG. 2 a). This result indicates that the sequencing-based microsatellite genotypes were accurate.

Calling Somatic Copy Number Alterations

To detect copy number events that co-occur with microsatellite instability, a new method to accurately measure copy number alterations was developed (Methods; FIG. 1 a). This feature leveraged the highly reproducible targeting performance of this approach [21]. It was observed that for any given DNA sample, the number of sequencing reads generated from an individual probe was highly reproducible across replicates and different DNA samples. Primers targeting the same genomic location had the same, consistent read count. In addition, it was observed that the ratio between read counts from the primers targeting the amplified or deleted regions will be different from other regions having no such changes. To determine copy number alterations, the read counts were normalized for systematic biases associated with GC content and the read counts. Those primers with greater variance in normalized count and thus performed with lower reproducibility were eliminated. Subsequently, the read count ratio was determined for each target gene and the ratio comparing the tumor to the matched normal genome was determined (Methods). Thus, a copy number was determined for each gene.

To validate the accuracy of the copy number measurements, the sequencing-based results were compared to other methods. A subset of samples was tested with digital PCR copy number assay for AURKA, CDK4, FLT3, VEGFA, ERBB2, FGFR1 and MET (FIG. 2 b). This comparison showed a high correlation between the MSI sequencing assay and digital PCR ($R^2=0.59$), supporting the accuracy of the present approach in copy number determination. In addition, WGS studies of seven sample pairs were conducted, and the targeted gene copy number changes had a high correlation with the WGS results ($R^2=0.77$; FIG. 2 c).

Profiling CRC Microsatellite Instability Across Different Sequence Repeat Motifs The extent of MSI across different categories of tandem repeats was determined. Among the 225 microsatellites that were sequenced, 129 of them had a somatic mutation leading to an allelic shift as detected in at least one CRC. A subset did not have any somatic mutations and allelic shifts; they were characterized by short repeat lengths and included mono- and dinucleotide repeats up to ten bp in length. In other words, all mono- and dinucleotide repeats longer than 10 bp had a mutation among the 46 CRCs. Nearly all of the other tri- and tetranucleotide repeat microsatellites (N=44) had at least one microsatellite mutation across the entire set of CRCs. The only exception involved the tetranucleotide repeat loci (D4S2364) which had no mutations. Interestingly, the microsatellite mutation fractions in mono- and tetranucleotide repeats demonstrated a high correlation ($r^2=0.90$), meaning that mutations in mono- versus tetranucleotide repeats were associated.

Figure 3:
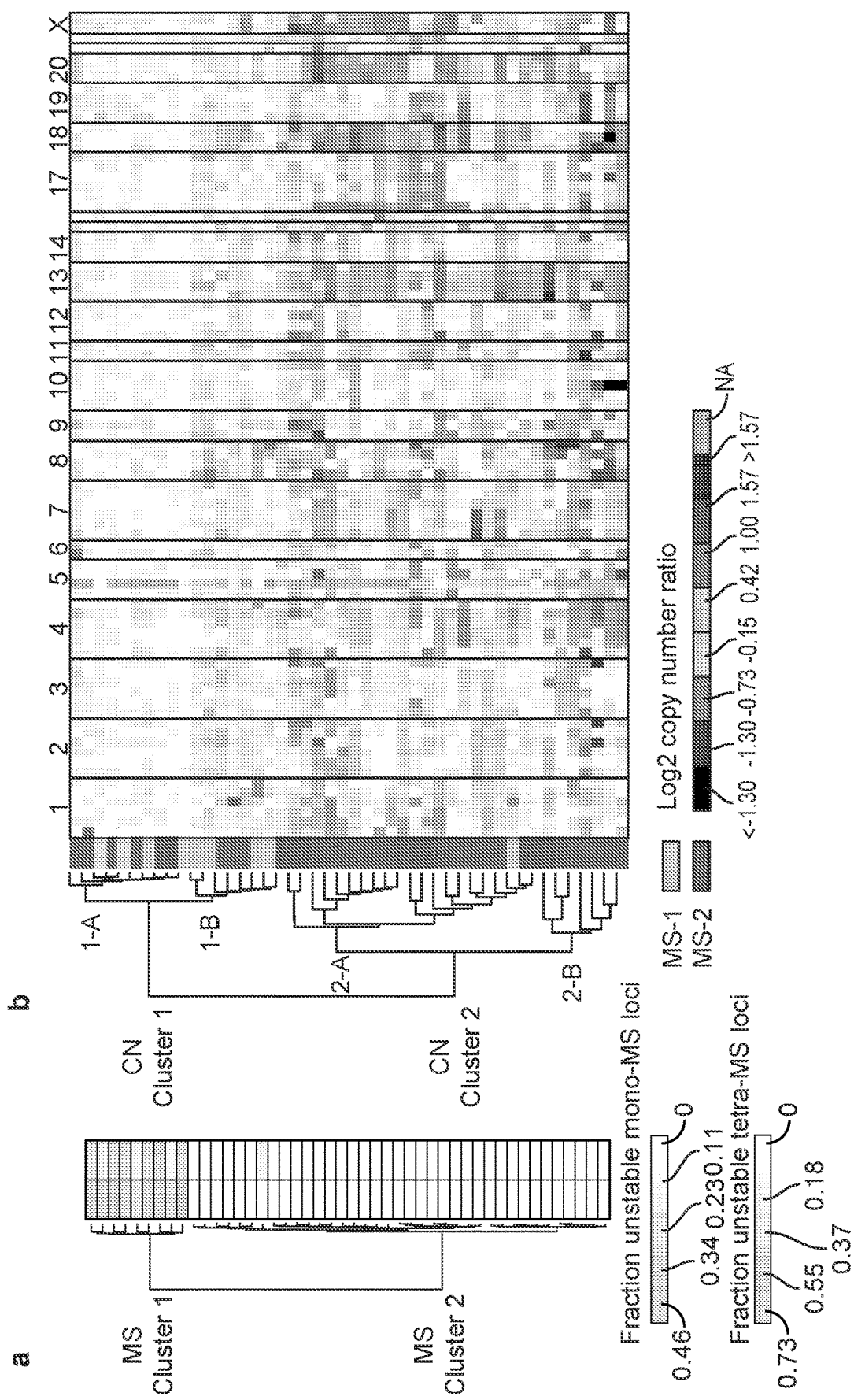
FIG. 3 a-c provides profiling diverse sequence tandem repeats and gene copy numbers in 46 colorectal cancers. (a) Clustering based on 225 microsatellites across four different classes. A 225×46 matrix including the presence (1) or absence (0) of microsatellite allele shift mutation was used for an unsupervised hierarchical clustering, which generated two clusters (MS Clusters 1 and 2). The heat map of the two microsatellite classes (mono- and tetranucleotide repeats) with the most contributions are shown in two separate columns. The mutation fraction in each class was calculated by dividing the number of somatic microsatellite mutations by the total number of genotyped microsatellites. (b) Clustering based on tumor/normal copy number ratio of 83 target genes. The median log 2 ratios for all the target genes were used for an unsupervised hierarchical clustering, which generated two major clusters. Each major cluster has two sub-clusters. In the first column of heat map, the MS Cluster identification for each CRC is indicated as different colors. The numbers on top of the heat map indicates the chromosome where the genes are located. Amplifications and deletions are indicated with red and blue colors, respectively. (c) Log 2 copy number ratio plots for all the CRCs having both MSI and CIN. For each CN index (x-axis), the log 2 copy number ratio between read counts from tumor and normal samples (y-axis) is plotted. The median ratio value is indicated with lines of black, red, or sky blue, representing no copy number change, amplification, or deletion, respectively. The integrated MSI and CIN status is indicated on top of plots, and the patient identifications at the left of plots.
Figure 3:
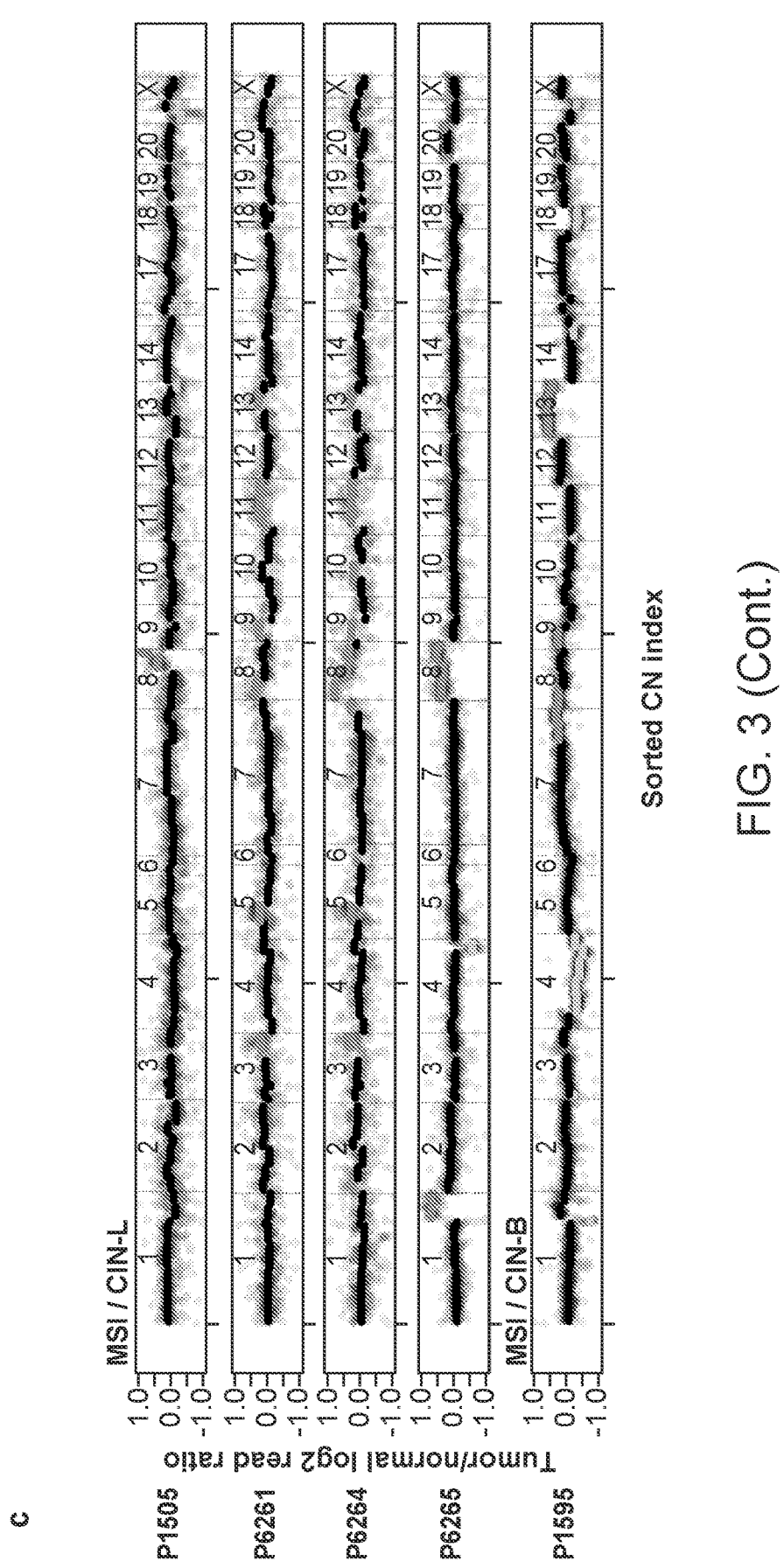

Next, an unsupervised analysis based on the microsatellite mutation profiles was conducted. The classification was compared to established molecular testing methods. As shown in FIG. 3 a, the hierarchical clustering extrapolated from MSI mutations identified two major groups: MS Cluster 1 (N=9) and MS Cluster 2 (N=37). All of the CRC samples in the MS Cluster 1 had a higher percentage of unstable microsatellite loci across all the classes of microsatellites than MS Cluster 2 (FIG. 3 a). Overall, the mean fraction of unstable microsatellite loci was 29.0% for Cluster 1 versus 1.2% for Cluster 2 which was statistically significant (p<0.001).

Among MS Cluster 1, all nine samples had elevated frequency of mutations present from 17.3 to 45.9% among the different mononucleotide repeats per each tumor. In addition, all of the Cluster 1 tumors had high frequency of mutations across the different tetranucleotide repeat mutations, ranging from 16.7 to 73.3% per each tumor. The analysis included 38 tetranucleotide repeats which is higher than any other reported study. Therefore, the results showed extensive association of mononucleotide and tetranucleotide repeat instability in CRCs. In summary, MS Cluster 1 CRC's had all the features of indicative of both MSI and EMAST.

For MS Cluster 2, mutations among the different classes of microsatellites was significantly lower. In this cluster, 25 out of 37 samples had mononucleotide repeat mutations. They ranged anywhere from 0.5 to 3.5% of this class of microsatellites per a tumor. Moreover, 22 out of 37 CRCs had low levels of tetranucleotide repeat instability. A range of 3.4 to 13.8% tetranucleotide repeats with mutations per tumor was observed. MS Cluster 2 CRCs had significantly lower levels but still had mutations in all classes as well.

Comparison With Conventional Detection for MSI-H and EMAST

From the same CRC samples, PCR and IHC assays were used for a conventional determination of MSI-H and EMAST status (Methods). The MSI PCR assay per the Bethesda criteria where MSI-H status requires two or more microsatellites to show size shifts based on somatic alterations was used. CRCs with only one microsatellite having a somatic size shift indicates MSI-low (MSI-L). Nine CRCs were MSI-H according to the PCR testing results. Eight of these CRCs from MS Cluster 1 had also undergone clinical IHC testing for the four MMR proteins (MLH1, MSH2, MSH6, and PMS2). All eight of these samples lacked MMR protein expression, which was consistent with the MSI status determined from the sequencing results. Then, a set of five tetranucleotide repeat (D20S82, D20S85, D8S321, D9S242, and MYCL1) previously used to determine EMAST status was tested [12]. If two or more show a size shift, this indicates EMAST instability. Eleven CRCs were classified as EMAST-positive. Finally, no tumors had evidence of MSI-L per PCR testing.

The PCR genotyping results were compared to the sequencing analysis. All nine tumors in MS Cluster 1 (sequencing) were positive for both MSI-H and EMAST PCR test. Overall, this result confirmed that the sequencing method was fully concordant with MSI-PCR. Thus, MS-Cluster 1 designated tumors with both MSI-H and EMAST. Again, this validation results suggests a general association of MSI-H and EMAST.

All of the tumors in MS cluster 2 were negative for MSI-H per PCR testing. This result was generally corroborated by the sequencing results where only small fraction of mononucleotide markers had somatic mutations. In addition, only a small number of CRCs that were EMAST positive were identified via PCR. Two CRCs (P544 and P685) were EMAST positive as denoted by somatic allelic shifts in two markers based on PCR analysis with capillary electrophoresis. However, when these results were compared to the sequencing analysis, both of the tumors showed relatively low levels of tetranucleotide repeat instability. Per the sequencing analysis, the P544 CRC had 7.1% of the tetranucleotide markers with mutations. The P685 tumor had even low frequency at 3.1%. Given that other studies have reported a much higher frequency of EMAST among CRCs, the results suggest that a greater number of tetranucleotide markers may be required to improve the sensitive and specific identification of these tumors for EMAST. 38 markers were used for this study. Another potential implication of these results is that EMAST may represent a mixed genomic instability state in CRC. Results supporting this possibility are presented later.

Based on comparing NGS to PCR testing, it was concluded that MS Clusters 1 and 2 were indicative of MSI and MSS status, respectively. Among this set of samples, none of the CRCs had MSI-L. In addition, no CRCs that were exclusive to EMAST or MSI-H were identified. Therefore, using this highly sensitive deep sequencing approach, the result show that MSI globally affects all classes of microsatellites.

The 3-Bp Shift Criterion Improves Specificity of MSI Classification

It was determined that microsatellite markers varied in their specificity for detecting MSI. From the sequencing results, reads covering the microsatellites markers used in conventional MSI PCR (NR-21, BAT25, BAT26, D2S123, D5S346 and D17S250) were examined. This set includes the entire Bethesda panel as well as three overlapping markers provided in a commercial set (Promega) (Table 4). The sequencing analysis detects any size of somatic indel shift compared to the matched normal tissue genotype, even as small as 1-bp. A 3-bp shift cutoff minimizes false positive detection due to PCR assay variation [33]. If the 3-bp shift criterion was applied to the sequencing results from the tumor, the Bethesda panel was as specific as the commercial assay in determining MSI. A previous report showed that dinucleotide markers included in the Bethesda panel were less specific for detecting cancer MSI [34]. However, the present results showed that the specificity of MSI detection improved with the 3-bp shift criterion when applied to dinucleotides markers.

TABLE 4

Frequency of allele shifts in traditional MSI markers

| STR ID | Panel | Motif | Frequency of all shifts | | Frequency of ≥3 bp shifts | |
|---|---|---|---|---|---|---|
| | | | MSI (n = 9) | MSS (n = 37) | MSI (n = 9) | MSS (n = 37) |
| NR-21 | Powerplex | A | 100% | 0% | 100% | 0% |
| BAT26 | Bethesda, Powerplex | A | 100% | 19% | 100% | 0% |
| BAT25 | Bethesda, Powerplex | T | 100% | 28% | 100% | 0% |
| D17S250 | Bethesda | GT | 100% | 29% | 67% | 0% |
| D5S346 | Bethesda | TG | 78% | 0% | 22% | 0% |
| D2S123 | Bethesda | CA | 67% | 0% | 56% | 0% |

Using the sequencing-based results, somatic indels of any size including 1 and 2 bp shifts were evaluated. Differences among the Bethesda markers that distinguish MSI were noticed. When considering somatic indels of any size, mutations in the NR-21, D2S123 and D5S346 microsatellites occurred exclusively in the MS Cluster 1 tumors (Table 4). The other three microsatellites (BAT25, BAT26 and D17S250) had indels mutations in both MS Cluster 1 (MSI/EMAST) and MS Cluster 2 (MSS) tumors. When the 3-bp criterion was applied, all five of the conventional Bethesda microsatellites identified only MSI tumors, thus increasing the specificity. However, this criterion reduced the sensitivity. For example, the D5S346 had microsatellite mutations in seven MSI tumors, but only two had a shift of 3 bp or more in size.

Notably, indel shifts of 3 bp or greater in length occurred only in MSI tumors, which was true not only in the microsatellites in the Bethesda panel, but also in all the mono- and di-nucleotide microsatellites included in the assay. In other words, only 1- or 2-bp allelic shifts for mono- and dinucleotide microsatellites were detected among the MSS tumors. Specifically, there were 27 MSS tumors with the microsatellite indel shifts smaller than 3 bp in size: 12 had at least two microsatellites that were affected; the remaining 15 had only a single affected microsatellite. These CRCs with small microsatellite allelic shifts may have a minor sub-population with an MMR deficiency, which is only detectable by a high sensitivity method, such as the present ultra-deep targeted sequencing assay. An example of such minor sub-population found in the P592 CRC is provided later with more details.

Analysis and Classification of Copy Number Alterations

Similar to the study of MSI classifications, a separate unsupervised clustering was conducted using only the copy number (CN) alterations from 83 targeted genes with the most reproducible copy number calling results. The analysis identified two major CN clusters (FIG. 3 b). CN Cluster 1 had a total of 18 CRCs and on average only 7% of genes had a CN. CN Cluster 2 had the remaining 28 CRCs which had a significantly higher number of CN alterations affecting 44% of the genes on average. The differences in CN between the two clusters was highly significant (p<0.001).

CN Clusters 1 and 2 had distinct sub-clusters (FIG. 3 b). CN Cluster 1 had two sub-clusters. The first one, CN Cluster 1-A (N=10), had copy number changes averaging less than 1% of the genes per a sample, which is in line with a chromosome-stable (CS) state. The second one, Cluster 1-B (N=8), had copy number changes evident in range of 6-26% of the genes across these samples, demonstrative of a lower level of chromosomal instability. This difference between the two subclusters was highly significant (p<0.001).

Likewise, CN Cluster 2 had two distinct subclusters. Cluster 2-B (N=7) had high-amplitude focal gene amplifications with six or more copies per gene or the presence of homozygous deletions. CN Cluster 2-A (N=21) had copy number changes that involved amplifications of broader genome segments that could extend over entire chromosome arms. A high focal amplification of MYC, a well-known oncogenic driver, occurred in P98 and P685 as noted by a log 2 ratio was greater than 2. The tumor suppressor gene, TP53, was one of the most frequently deleted genes (N=21), as has been observed among other studies [35]. In addition, a series of chromosome-wide events (i.e. amplification or deletion in all the target genes across the arm of a given chromosome) were identified. For example, chromosome wide amplification of Chromosomes 13 (N=16), Chromosome 20 (N=17) and deletion of Chromosome 18 (N=21) were the most frequent among the all of the CRCs.

Designating Classes of Chromosomal Instability

To determine if the hierarchical clustering analysis was related to different categories of CIN, a multi-class statistical model based on the copy number alterations for the targeted 83 cancer genes was used. For training, copy number information from the TCGA CRC copy number dataset (N=339) using the same genes from the present panel was used. A previous study from Liu et al. of colorectal cancer identified specific classes of CIN involving either focal (CIN-F) versus broad (CIN-B) genomic changes [36]. In this report, the size and amplitude of events were summarized by a score. A statistical threshold was used to define the two major classes. CIN-F was characterized by high amplitude focal amplifications whereas CIN-B had low-amplitude amplifications that spanned broader segments of the genome. This class included tumors where copy alterations covered entire chromosome arms.

For the study, the 83 gene classifier was trained using TCGA CRC results from the study of Liu et al. Then, it was determined how the hierarchical CIN clustering (Cluster 1 and 2) overlapped with the CIN states (i.e. CS, CIN-F, and CIN-B) defined by Liu et al [36]. The sensitivity and accuracy of the model was evaluated by performing five-fold cross-validation. The model had an overall prediction accuracy of 100% (sensitivity 1, specificity 1), indicating that the CIN cluster results overlapped precisely with the CIN-B and CIN-F states based on the TCGA data set. Additionally, when the training data and validation TCGA datasets were reversed, the same level of sensitivity and specificity was found. Thus, it was concluded that CN Clusters 2A indicated CIN-B while CN Cluster 2B indicated CIN-F.

In terms of CIN Cluster 1, a distinct subset was observed. Cluster 1-B had a significantly higher number of affected genes than Cluster 1-A. In addition, the amplitude of copy number changes in Cluster 1-B was significantly higher than that in Cluster 1-A; the difference was measured by comparing the variances of log 2 gene copy number ratios ($p<0.001$). Given this significant difference, CRCs in CN Cluster 1-B were classified as chromosome instability low (CIN-L), an indicator of the low degree of copy number changes. The remaining CRCs were considered to be chromosome stable (CS).

MSI and CIN Co-Occurrence in CRCs

As it was established that the present sequencing-based profiling of microsatellites and cancer genes accurately detected various MSI and CIN classes, the next step was to determine whether there was evidence of co-occurrence of these genomic instability states. Among the nine CRCs with MSI, five had evidence of co-occurring copy number alterations and thus, indicators of CIN. Four CRCs (P1505, P6261, P6264, and P6265) had both MSI and CIN-L (FIG. 3 c). Interestingly, all four tumors had amplifications among four genes WRN, FGFR1, TRPS1 and MYC which are located on Chromosome 8. No deletions were noted among these genes.

In contrast, MSS CRCs had both amplifications and deletions among these same Chromosome 8 genes. Specifically, there were 31 MSS tumors with CIN-L, CIN-B or CIN-F. Nineteen of these tumors had at least one deletion among the four genes on Chromosome 8. Notably, majority of the deletions occurred in the genes on the 8p arm; fourteen of the MSS tumors had no deletion in the genes located on the 8q arm, but only in the genes on the 8p arm.

One tumor had a striking and distinct pattern of mixed genomic instability. The P1595 CRC was MSI/CIN-B. This tumor had the highest number of chromosome-wide copy number changes among the MSI CRCs (FIG. 3 c). Amplifications were found among the genes in Chromosome 8 and 13 as well as deletions in Chromosomes 4 and 18. This pattern matched those of the CRCs which were microsatellite stable and CIN positive. This combination of genomic instability features would have been missed with conventional MSI PCR testing. Very few if any CRCs have been examined for this combined genomic instability phenotype.

Liu et al.'s result from their TCGA CRC study was examined; there were multiple examples of tumors with MSI-H and CIN broad or focal copy number alterations [36]. Other studies have noted similar observations where 26-61% of MSI CRCs have copy number alterations or features chromosomal instability. [37-44]. These other studies used conventional assays including karyotyping, fluorescent in situ hybridization, flow cytometry for aneuploidy, array comparative genomic hybridization (CGH) and oligonucleotide arrays. Although these studies used different platforms, if one aggregates all of their samples (N=248), 41% (N=101) showed mixed MSI and CIN features. Given that none of these studies used genome sequencing to define copy number, these previous reports may underestimate the prevalence of mixed instability classes. Moreover, they lacked the resolution of delineating specific genomic features which cancer NGS methods provide.

Tumor Mutations and Overlap with Genomic Instability States

Figure 4:
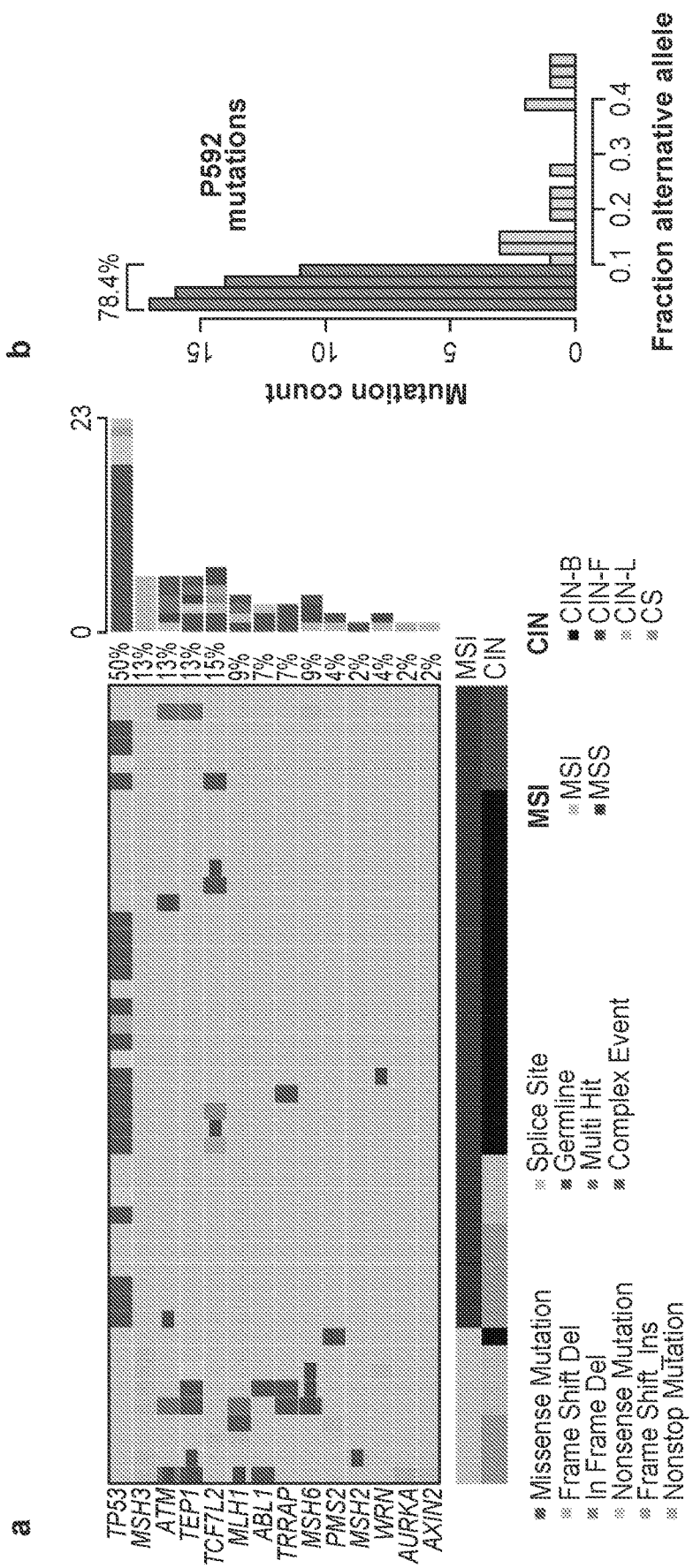
FIG. 4 a-b provides mutation profile for genes related to DNA maintenance. (a) Oncoplot for the DNA maintenance genes. For all the genes related to DNA maintenance (rows), mutation profiles of 46 tumors (columns) are shown. Only the mutations with a CADD score greater than 20 are used. Different types of somatic mutations are shown as rectangles with different colors. Gray color indicates that there is no mutation call at a given gene. Germline mutations are also indicated with a shorter rectangle overlaid on the somatic mutation map. Right panel shows the number of affected samples for each gene. Genes are sorted according to the frequency of somatic mutations. Lower panel indicates MSI and CIN sample annotations determined by the sequencing assay. (b) Distribution of alternative allelic fractions in the P592 tumor. The mutations with an allelic fraction less than 0.1 are indicated with red color, and the percentage is also provided on top of the corresponding histogram bars.

From the deep sequencing of the cancer genes, mutations including substitutions and indels among well-established CRC driver genes were identified. As one would expect, the MMR genes (e.g. MLH1, MSH2, MSH3, MSH6, and PMS2) had different mutation frequencies when comparing the MSI versus MSS CRCs (FIG. 4 a). All the nine MSI CRCs had at least one somatic mutation in MMR genes. Six of the MSI CRCs had germline mutations of MMR genes, and four of them also had a somatic mutation at the gene with a germline hit. The only MSS tumor with a MMR mutation was P592, which had a somatic mutations in MSH6 as is described in more detail later.

The 16 genes (MSH2, MSH3, MSH6, MLH1, PMS2, ATM, TP53, WRN, TRRAP, AURKA, TEP1, etc.) which play a role in DNA repair and genome stability, were examined (Table 3). The results included the following: 10 genes had frequent mutations among the MSI tumors; three genes had mutations in both MSI and MSS, and one gene had a mutation among the MSS tumors. Notably, MSI tumors had no mutations in TP53 versus 62.2% of MSS CRC had mutations.

A MSH3 indel was found to be a hotspot mutation among the MSI tumors (66.7% in MSI versus none in MSS). This recurrent indel was at an adenine mononucleotide repeat, located at exon 7 of MSH3; this mononucleotide homopolymer is described as being eight bases in the genome reference). Interestingly, MSH3's mutation allelic fraction had a general correlation with the extent of MSI observed in tetranucleotide repeats. Among the five CRCs with MSI and CIN, MSH3 mutations were found in four tumors. As noted, when consider those CRCs with a MSH3 mutation, the allele fraction of the MSH3 mutation had a positive correlation with degree of EMAST. MSH3 mutations did not overlap with TP53 mutations. A similar level of exclusivity was evident among other sets of CRCs including those analyzed in the TCGA study where among 323 CRCs with a mutation in either, 95% being exclusive to one or the other [31].

A notable example of mixed genomic instability states was evident in the P592 tumor. This CRC was MSS per the sequencing analysis and the MSI PCR test results. However, this CRC had 74 mutations, which was even higher than the average mutation count of MSI CRCs (43 mutations) that normally hypermutable. It was observed that 80% of P592 CRC's mutations occurred at a lower allelic fraction of 10% or less. This lower mutation allele fraction represented a subclonal population of tumor cells (FIG. 4 b). Interestingly, a mutation was discovered in MSH6 that was present at a somatic allelic fraction of 6.3% and lead to a frameshift. Among all of the MSS tumors, this CRC was the only one with a mutation in the MMR genes. A copy number loss per a log 2 ratio of −0.11 was also noted. This was a lower value that is attributed to the deletion being a in a small proportion of tumor cells. Moreover, this was one of the MSS tumors that had many small somatic shifts (i.e. 1 or 2 bp) in mono- and dinucleotide microsatellites as determined through deep sequencing. These lower fraction mutation in this tumor were detected because of the very high sequencing coverage (3,366×) of the target cancer genes and microsatellites. Taking all of these observations into account, these results are consistent with biallelic somatic events in MSH6 that occurred in subclonal population. It is posited that the tumor cells in this subclone were then subject to a greater level of hypermutations consistent with MSI tumors while maintaining CIN features in parallel among the other clones. This result is another indication suggesting that MSI-L state per the MSI PCR test may reflect a subclonal population of cells with DNA MMR loss.

Subclonal Structure of CRCs with Joint MSI and CIN

Figure 5:
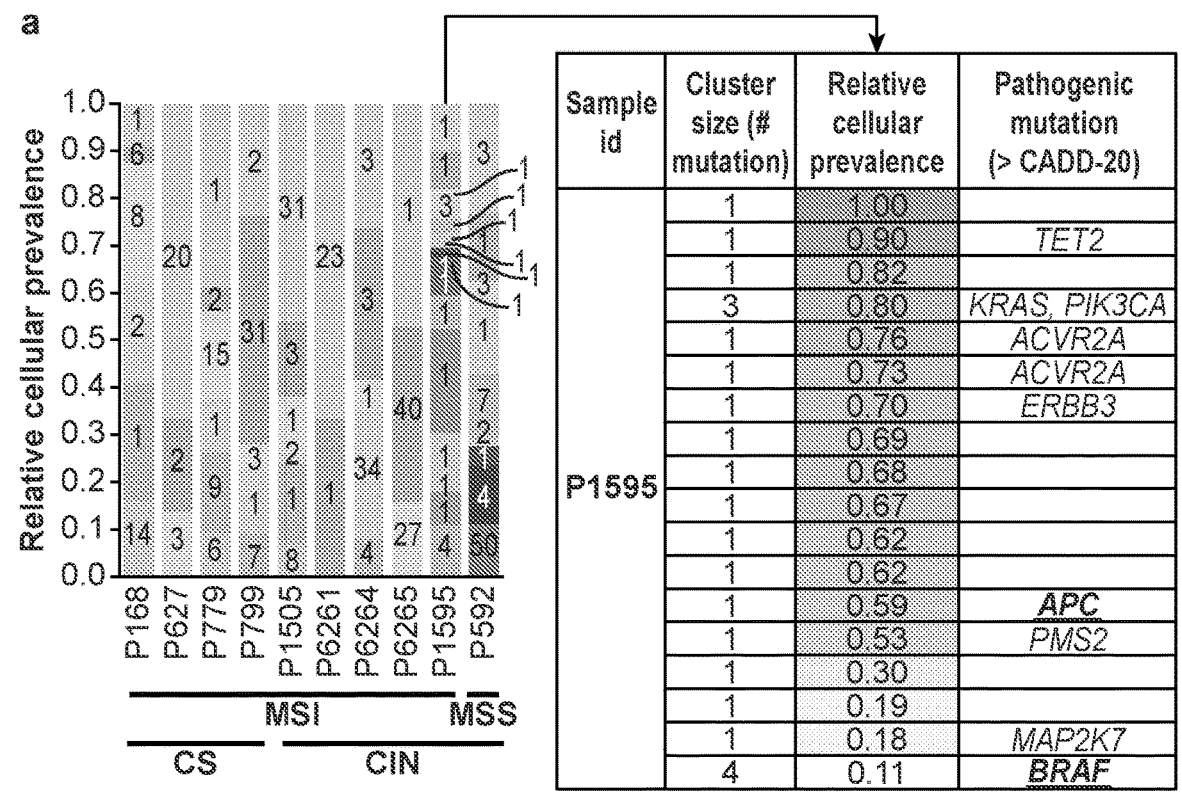
FIG. 5 a-b provides clonal diversity of hypermutated tumors. (a) Clonal diversity analysis for hypermutated tumors. Relative cellular prevalence of each clone, indicated by overlapping bars in the plot, was estimated by PyClone based on allelic fraction of the mutations shared by each clonal population. The number of mutations for each clone is indicated at the inside of each bar. MSI and CIN status determined by the unsupervised analysis are indicated at the bottom. For the P592 tumor, the pathogenic mutations included in each clone are also provided in the table next to the bar plot. The underlined gene mutations (APC and BRAF) are generally known to be exclusive. (b) Clonal diversity shown in MSI analysis. For a microsatellite locus (NR-21), allele profiles of both normal and tumor samples from P1595 are shown. Electropherograms generated by PCR-CE method (left panels) provide relative abundance (y-axis, fluorescence intensity) of amplicons with different sizes (x-axis, DNA size in bp). Although it has stutter amplification which represents an artifact, the tumor allele profile suggests many different allele shifts (i.e. two or more), matching the observation from the mutation-based clonal diversity analysis. The allele histograms generated by the deep sequencing approach (right panels) provide relative abundance (y-axis, sequencing read count) of DNA molecules, including different microsatellite alleles (x-axis, number of motif repeats). From the normal allele profile, the homozygote allele (23 motif repeats) is apparent. On the other hand, from the tumor allele profile, many different allelic shifts are observed, also strongly supporting the clonal diversity. Given that no PCR amplification was used, these allele shifts were not results of erroneous stutter amplification but rather represented true somatic allelic shifts from mutations among different clones.
Figure 5:
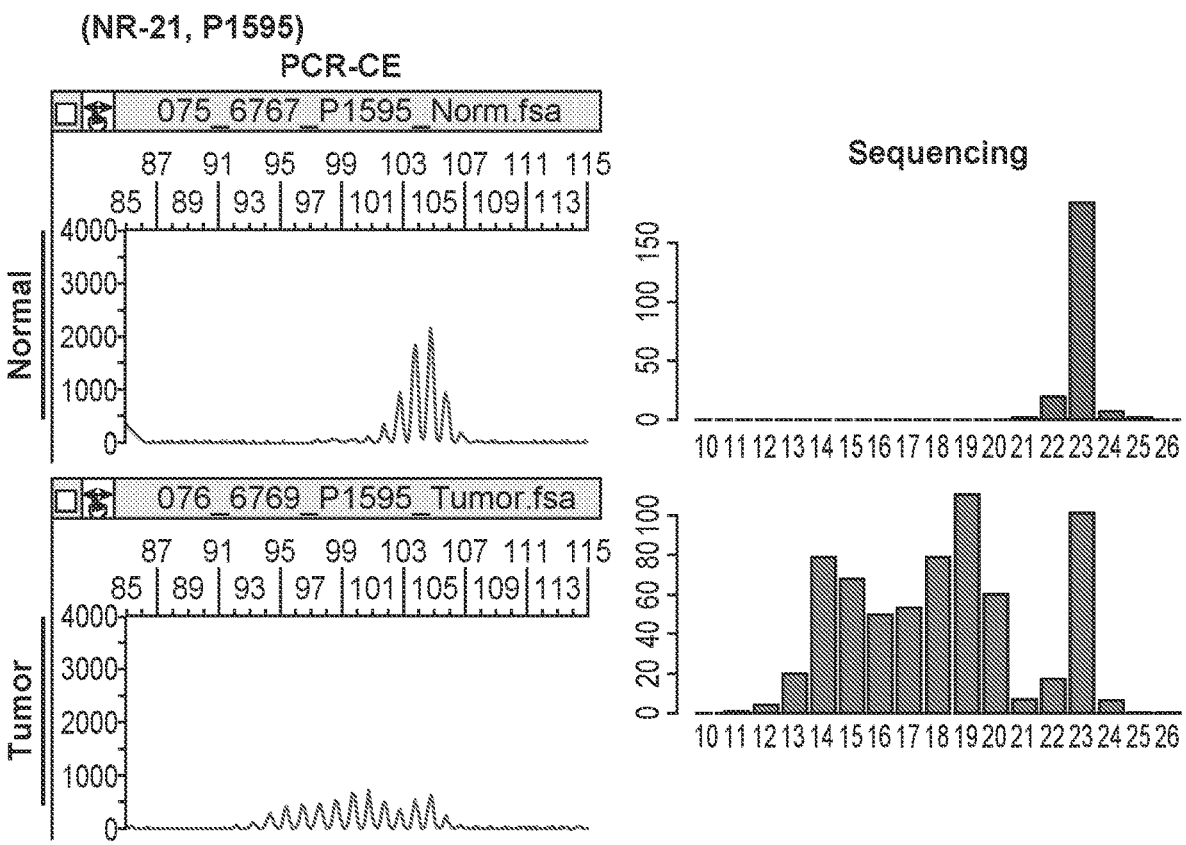

The subclonal structure and the relative population sizes were determined among the nine CRCs with MSI (FIG. 5 a). The results revealed a diverse range of tumor cellular architecture types across MSI CRCs. For this analysis, PyClone was used; this algorithm relies on targeted sequencing data with high coverage, deconvolutes the clonal architecture of tumors and estimates the subclonal cellular prevalence of somatic mutations [45].

For any given MSI tumor, different levels of subclonal diversity, which can be inferred by the number of mutation clusters, were observed. All nine CRCs had two or more clones as defined by groups/clusters of mutations with similar degrees of cellular representation. Among the CRC mutations that were pathogenic (i.e. variants with a CADD score greater than 20), specific patterns were noted in terms of their clonal clustering distribution. Deleterious mutations generally occurred in larger sizes than the clusters without pathogenic variants (mean values: 1.5 versus 11.6 variants per cluster, $p<0.001$). A range of subclonal heterogeneity was observed across the MSI tumors with CIN. For example, the P6261 CRC (MSI/CIN-L) had only two mutation clusters; the cluster with largest size included 96% of the mutations.

The P1595 CRC (MSI/CIN-B) had 18 distinct mutation clusters, where the largest cluster contained only 17% of the mutations. Among the MSI tumors, this CRC had the highest level of clonal diversity as well as the highest number of copy number alterations. The high clonal diversity of P1595 CRC was also confirmed by the heterogeneity of tumor microsatellite alleles (FIG. 5 b). A pentanucleotide repeat marker, which is part of the commercial MSI PCR kit (Promega), showed five different alleles in P1595 CRC. In contrast, the P799 CRC, with less clonal diversity, had relatively homogeneous tumor microsatellite alleles.

Subclonal Co-Occurrence of BRAF and APC Driver Mutations in a MSI Tumor

The CRC from P1595 (MSI/CIN-B) had pathogenic mutations in both APC and BRAF (FIG. 5 a). Somatic mutations in these two cancer drivers are generally exclusive, meaning that CRCs do not typically possess both mutations [46]. Notably, this tumor had both APC and the BRAF mutations identified in separate sub-clones based on their size. The APC mutation was in a mutation cluster with a cellular prevalence of 0.59, while the BRAF mutation in a mutation cluster with a cellular prevalence of 0.11. In addition, APC had a copy number change indicative of a deletion. Thus, it was extrapolated that the APC demonstrate a loss-of-function, providing a truncal cancer driver with the BRAF mutation appearing later in a subclonal population during the course of tumor evolution. This result suggests a dramatic divergence in this tumor where distinct genomic instability and driver pathways differentiated clonal subpopulations in a MSI tumor.

Whole Genome Analysis of MSI CRCs

Figure 6:
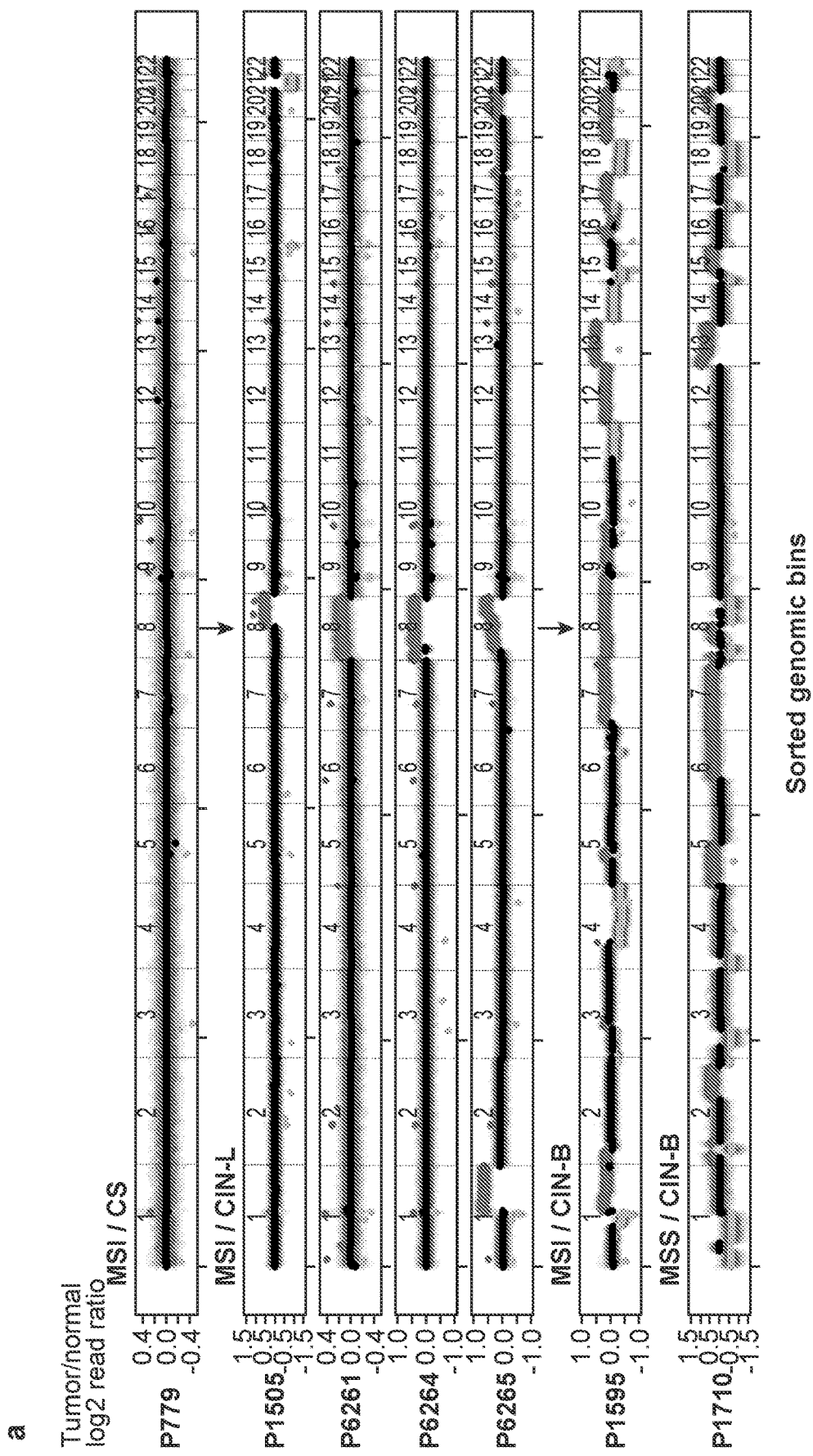
FIG. 6 a-b provides genome-wide copy number changes in MSI tumors determined by WGS analyses. (a) Log 2 copy number ratio plots from the WGS analysis. This analysis included all five MSI/CIN samples, as well as one MSI/CS and one MSS/CIN samples as controls. For each genomic bin (x-axis), the log 2 copy number ratio calculated by CNVkit (y-axis) is plotted. The log 2 ratio value of genomic segments is indicated with lines of black, red, or sky blue, representing no copy number change, amplification, or deletion, respectively. The dotted vertical lines separate genomic bins from different chromosomes. The integrated MSI and CIN status is indicated at the top of the plots, and the patient identifications at the left of plots. (b) Validation of chromosome arm-wide copy number events in MSI tumors using TCGA CRC samples (N=617). Separately for MSS/MSI-L and MSI-H tumors, frequencies of copy number gain and loss are shown for each chromosome arm. Gains are shown above and losses below the labels of chromosome arms.
Figure 6:
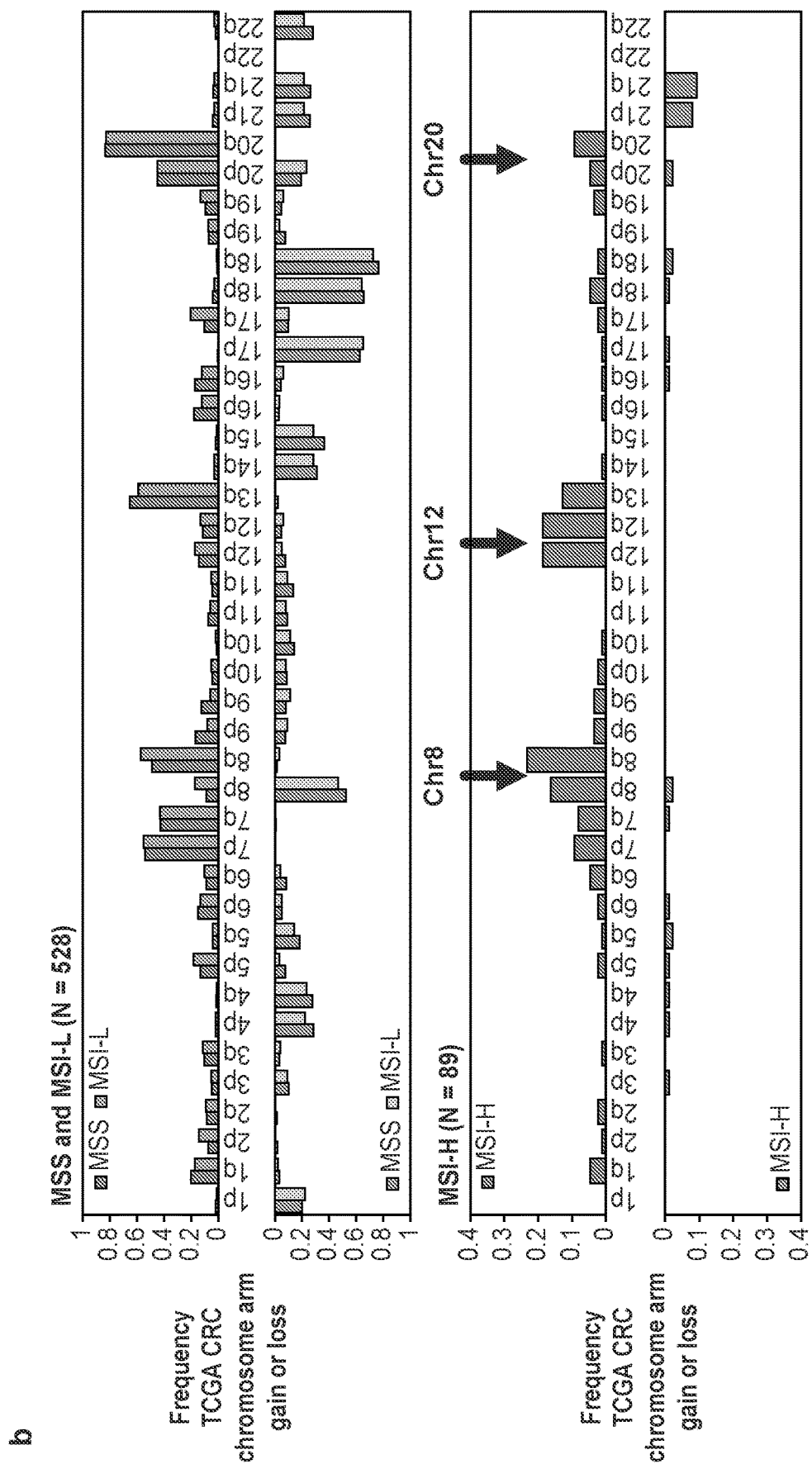

Whole genome sequencing was applied to five CRCs (P1505, P6261, P6264, P6265, P1595) with mixed genomic instability features and two CRCs (P779 and P1710) with only one class of genomic instability (FIG. 6 a). Specifically, the P779 CRC was MSI/CS and the P1710 CRC was MSS/CIN. To improve the detection of rearrangements, linked read sequencing were used on a subset of samples (P779, P1505 and P1595). The remainder used conventional WGS. As previously published, linked read sequencing uses molecular barcodes to identify and characterize single high molecular weight (HMW) DNA molecules up to 0.2 Mb in size, if not larger [47]. Using the long-range genomic information from those individual HMW DNA molecules, cancer rearrangements are detected with improved sensitivity, complex structural alterations are characterized more readily and Mb-scale haplotypes are revealed, some of which span entire chromosome arms [47, 48-50]. Samples had high quality HMW DNA molecules, typically in a size range of 20-30 kb on average. The HMW DNA provided phased haplotype blocks of 0.5-4.6 Mb in size.

First, the WGS and targeted sequencing calls were compared for copy number alterations. A genome wide metric involving the fraction of segments with a copy number change over the entire breadth of the genome was considered. Comparing the two results demonstrated concordance across all samples. The targeted sequencing classification of CIN exactly matched the WGS results. The CIN-B tumors (N=2) had at least 37% or greater of their genome covered by copy number alterations. The CIN-L tumors (N=4) had 5% or greater of their genome affected by copy number changes. Importantly, the CRCs with CIN-L (P1505, P6261, P6264, P6265) had a consistently higher degree of genomic instability than the P779 CRC with MSI/CS which was consistently diploid in its profile.

Chromosomal instability events included increased copy number changes that encompass either one or both arms of a chromosome, the latter being an example of aneuploidy. Such broad genomic copy number changes were observed in all of the MSI/CIN-L tumors—this WGS result confirmed what was observed in the targeted sequencing analysis (FIG. 6 a). For example, the P6265 CRC (MSI/CIN-L) had a copy number increase in chromosome arms 1q, 8q and both arms of 20, indicating aneuploidy of this chromosome. P1505 had a copy number increase in chromosome arm 8q and loss of a both arms in chromosome 21. Overall, the WGS results point to the presence of notable levels of chromosomal instability in primary MSI CRCs.

Chromosome 8 Copy Number Increase Among MSI CRC Tumors

Among the CRCs analyzed with WGS, amplifications in Chromosome 8, which corroborated results from the deep sequencing analysis, were detected. All five of the MSI/CIN tumors (P1505, P6261, P6264, P6265 and P1595) had an amplification of the chr 8q arm (FIG. 6 a). The P6261 and P1595 CRCs demonstrated an increase across all of Chromosome 8, indicating aneuploidy. The P6264 CRC also had features indicative of Chromosome 8 aneuploidy albeit with a large segment of the Chr8p arm being diploid. P6265 had even more complex features with the telomeric segment of 8p being diploid, an increased copy number segment crossing over p and q arms and an even greater increase in the 8q telomeric segment. In contrast, the P779 tumor, classified as MSI/CS per the targeted analysis, showed no significant changes in its diploid chromosome complement.

To validate the observation among a larger number of tumors, the TCGA CRCs (N=617) and their genomic copy number data were examined. Based on the CN profiles, the status of chromosome arm copy number was determined (Methods). It was determined that chr 8q amplification was very common among MSI-H tumors (N=89) with 23% (N=21) having evidence of this event (FIG. 6 b). In addition, 16.3% of TCGA MSI CRCs had an increase in the 8p arm copy number. Likewise, MSI CRCs had frequent copy number alterations affecting Chromosomes 7, 12, 13 and 20. Regardless, the most frequent change was observed in the chr8 q arm.

Several other studies that validated these findings with different methods were identified. Using metaphase CGH, Camps et al. identified that 36% (N=5) among a set of MSI CRCs (N=13) had a chromosome 8 copy number increase [39]. Trautmann et al. used array CGH and determined that copy number increases in the locus was 8q22-24 was the most commonly observed event among 35% (N=8) among a set of MSI CRCs (N=23). Overall, these studies provided independent corroboration of the results point to the prevalence of Chromosome 8 copy number increases among MSI tumors.

Chromosome 8 Translocation in a MSI CRC

Figure 7:
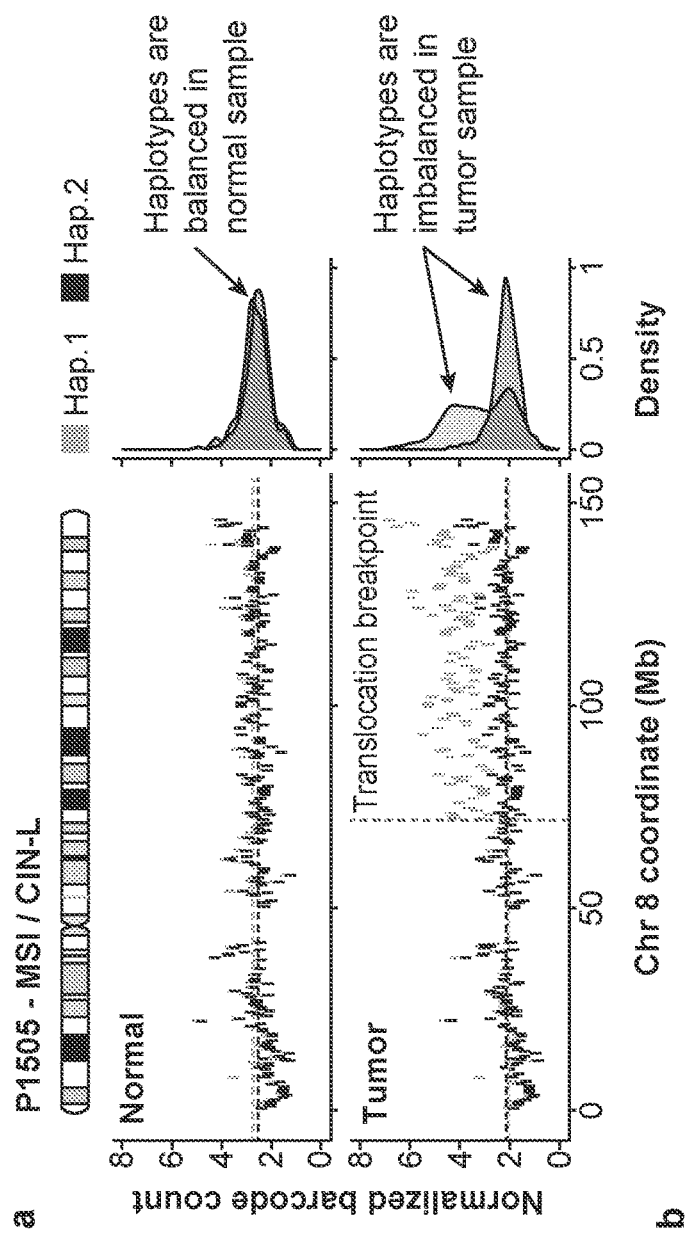
FIG. 7 a-b provides inter-chromosomal rearrangement in a CRC tumor with a mixed MSI/CIN phenotype. (a) Haplotypes of chromosome 8 in the normal and tumor samples of P1505. The blocks indicate the original fragmented haplotypes determined by linked-read sequencing, and their color denotes their subsequent assignment to haplotypes covering many Megabases. Haplotype 1 (blue) in the tumor sample displays an allelic imbalance on chromosome 8q that reflects an amplification event, beginning at the translocation breakpoint with chromosome 15. The density plots to the right reflect the distribution of the haplotype counts. (b) The translocation event from the tumor sample of P1505 (a MSI/CIN-L tumor). For the CIRCOS plot (right), an inter-chromosomal change is indicated with an orange line. Chromosomes are indicated as curved boxes along the circle, where the chromosome 1 starts from 12 o'clock direction, and expands towards the clockwise direction. The width of the box represents the size of chromosome. Inside the boxes, the log 2 copy number ratio from genomic segments is shown as a heat map, where orange and blue colors indicate amplification and deletion, respectively. The positions where an amplification at Chromosome 8 and a deletion at Chromosome 15 start coincide with the translocation breakpoints. As shown in the left panels, molecular barcodes from linked read sequences are found in two genomic regions flanking the breakpoints of translocation. Each row indicates individual DNA molecules that are found in both the genomic regions. The alignment of barcoded reads is indicated by horizontal lines located at the genomic positions (x-axis).
Figure 7:
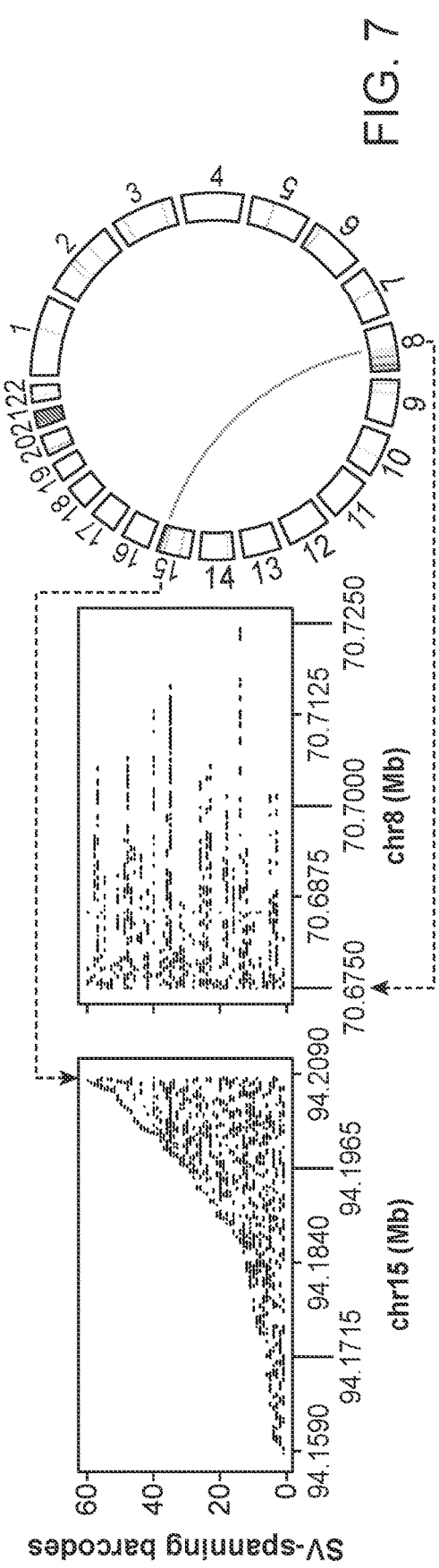

With linked-read WGS, an inter-chromosomal rearrangement event in the P1505 CRC (MSI/CIN-L) was discovered (FIG. 7). Linked read sequences are used to identify chromosome arm alterations that are assigned a specific haplotype. Cancer allelic imbalances increases the copy number representation of a specific haplotype. Using linked read sequencing from normal tumor pairs, it can be determined if a chromosome arm has been involved in a duplication event that increases the ratio of one haplotype to another [48]. Referred to as digital karyotyping, this analysis produces information similar to conventional karyotyping or FISH but also has the advantage of having the resolution of whole genome sequencing. After conducting this haplotype analysis, it became clear that a specific haplotype of Chr 8q had been duplicated, with increase in a specific imbalanced haplotype which pointed to a specific breakpoint in the q arm proximal to the centromere (FIG. 7 a).

On closer analysis of this breakpoint, a novel translocation between Chromosomes 8 and 15 that has never been reported in colon cancer was identified (FIG. 7 b). The breakpoints were located at 8q13.3 and 15q26.2 and, and the Chromosome 8 breakpoint separates exons 2 and 3 of XKR9. This gene is a cell membrane bound protein and a member of the Kell Blood Group complex subunit-related gene family [51]. Based on a National Library of Medicine Pubmed literature search during the submission of this manuscript, there were no articles describing functional studies of this gene. One recent article reported that XKR9 gene expression in cancer was associated with decreased overall survival [51]. In this report, Li et al. used the TCGA genomic data from 21 cancer types and identified differential expressed genes in tumors originating from different ethnicities. XKR9 differential expression had the most significant association with survival. Another reported identified recurrent deletions in 8q13.3 locus that are causative for Branchio-Oto-Renal syndrome [52]. The deletion breakpoints involved human endogenous retroviral sequences and the authors hypothesized that these repetitive elements mediated a recombination lead to recurrent deletions causative for this genetic syndrome. Overall, the result suggests that Chromosome 8 has a predilection for CIN among MSI CRCs. P1505 CRC had the MSH3 frameshift with the highest allelic fraction (84.6%) among all MSI tumors. One possibility is that the MSH3 mutation was an early mutation during cancer development or provided a fundamental selective advantage that allowed this clone to become dominant.

DISCUSSION

An ultra-deep sequencing approach for characterizing somatic alterations of microsatellites and copy number changes in cancer was developed. An integrative analysis of genomic instability features on CRCs was conducted. Unlike nearly all studies examining microsatellites, different classes of MSI markers were examined for somatic changes, and thus quantitative instability levels were determined, not only in mono- and di-nucleotide repeats, but also in tri- and tetra-nucleotide markers. Tri- and tetranucleotide repeats are generally excluded from short read sequencing-based analysis; they are too lengthy for most targeting assays using short reads [7]. Moreover, the targeted assay can measure copy number changes with a precision comparable to whole genome sequencing. Generally, targeted sequencings such as whole exome sequencing are not considered ideal for copy number analysis [53], but the approach proved to be particularly robust as it was validated with a variety of other methods including digital PCR and whole genome sequencing.

MSI status was assigned for tumors having instability in all the MS classes. These MSI tumors showed distinct characteristics: i) The MSI tumors had varying degrees of microsatellite mutation with both mono- and dinucleotide repeats being proportionally elevated along with tri- and tetranucleotide repeat alterations; ii) some MSI tumors showed CIN with chromosome- or chromosome arm-wide copy number changes as well as a translocation; iii) Quantitative MSI profiling across larger number of microsatellites as well a deconvoluting subclonal populations, revealed examples of MSI subclones coexisting with other subpopulations that did not have as elevated mutations rates.

Traditional PCR tests sometimes lead to a classification of 'low' status, generally defined as positive only in a portion of markers. (e.g. MSI-L, EMAST-L). Like the traditional MSI tests, PCR tests for EMAST tumors also use only five or more markers [12-14, 54]. Some recent studies used a commercial assay using 16 forensic markers [15], but the expanded number lead to a new designation of EMAST-L tumors, i.e. inconclusive between positive and negative. In the study, with an expanded number of tetranucleotide markers, there was definitive result about the extent of EMAST and this EMAST-L was not identified. The results suggest that a wider range and greater number of tetranucleotide markers are important for accurate determination of EMAST.

The present study showed that the MSI tumors had different microsatellite mutation fractions in a range. Although with a limited resolution, the MSI PCR test using five mononucleotide markers also generated results matched to the microsatellite mutation fraction measured by the sequencing analysis ($R^2=0.95$; FIG. 2 a). A recent study about genetic heterogeneity of MSI tumors revealed that the overall genomic MSI level, termed 'MSI intensity' in the study, is a predictor of response to immunotherapies [55]. Given the clinical implication, an improved MSI test should determine not only positive versus negative, but also the quantitative extent of MSI. The precise quantification of genomic MSI level will optimize patient care decisions, and the present microsatellite assay provides this feature.

MSI markers were separated into two groups according to their repeat motif length (mono- and di-nucleotide repeats versus tri- and tetra-nucleotide repeats), and then microsatellite mutation rates within each group were compared. There was a clear correlation between length of microsatellites and the mutation frequency across all tumors regardless of their MSI status. This result shows that many MSI markers are not specific, especially when their length is long. All the traditional microsatellite markers are relatively long (>20 bp), and some of them were frequently mutated even in MSS tumors (Table 4). To be both sensitive and specific in MSI detection, any molecular test should include more markers with enhanced specificity (e.g. markers with intermediate length).

Another noteworthy feature of MSI tumors was that the microsatellite mutation fractions in mono- and tetranucleotide repeats were highly correlated ($r^2=0.90$). Therefore, all the MSI tumors unstable in mono- and dinucleotide repeats were also unstable in tri- and tetranucleotide repeats. CRCs with instability limited to mono- and dinucleotide repeats or to tri- and tetranucleotide repeats were not identified. Most studies reported tumors with only a single type of instability (i.e. MSI-H only or EMAST-positive only), which were as frequent as the tumors having both types of instability [12-15, 54]. The PCR tests can generate false positives depending on the marker choices. The original Bethesda marker set (two mononucleotide and three dinucleotide repeats) were revised because the tumors having MS shifts only in dinucleotide repeat loci were frequently false positives [34]. However, the dinucleotide markers are still being used when determining MSI status [14, 54]. Moreover, there is no standardized set of markers for EMAST. A set for EMAST was used for the samples, and two false positives were identified. In summary, the tumors identified by PCR tests as having only one type of MSI may be false positives.

The presence of an EMAST phenotype in MSI-H tumors has not been examined. It is thought that a major driver of EMAST in MSS tumors is MSH3 loss-of-function. Changes in MSH3 cellular location rather than deleterious mutations or epimutations are the basis of this change in function [11]. However, MSI-H tumors also have a propensity for acquiring pathogenic indel mutations in MSH3 [56]; in the study six of nine MSI tumors had this MSH3 indel and the mutation allelic fraction had a positive correlation with the fraction of tetranucleotide repeat loci having a MS allele shift. This suggests that those MSI tumors may have acquired a later MSH3 mutation which elicits an EMAST phenotype in subclonal population. One or two bp deletions in the MSH3 homopolymer results in frameshift in protein expression, and eventually, increased microsatellite mutation rate in tetranucleotide repeats. In summary, the present study shows that MSI-H tumors are likely to acquire EMAST phenotype as a result of the initial instability in mononucleotide repeats.

Generally, it is thought that dysfunction among different DNA repair mechanisms leads to exclusive states of genomic instability, such as MSI or CIN. Two previous studies using array CGH had identified co-occurrence of MSI and copy number alterations [40, 44]. These studies were not sequencing based when determining the copy number status of the genome. As a result, they did not identify tetranucleotide repeat instability in relationship to different classes of CIN. In the present study, the majority of MSI tumors had CIN features (four CIN-L and a CIN-B), indicating a mixed genomic instability state. The extent of chromosomal instability seen among these mixed states tumors were significantly higher than CS tumors. Specifically, chromosome arm changes and aneuploidy were clearly evident, especially in Chromosome 8. Interestingly, all of the MSI/CIN-L tumors had a frameshift mutation in MSH3, which also supported the new classification. Change in MSH3 function creates double strand breaks, leading to chromosomal rearrangements [11]. In line with the MSH3's functional role in DNA maintenance, the tumor with the highest MSH3 allele fraction (P1505) in the study had an inter-chromosomal rearrangement event (FIG. 7). The only MSI tumor with CIN-B did not have the MSH3 frameshift, which may suggest that MSH3 dysfunction is only responsible for MSI/CIN-L overlap, not MSI/CIN-B. Overall, these unexpected structural rearrangements in MSI tumors suggest the presence of genomic heterogeneity of CRC tumors. Therefore, to be more precise in assessing the genomic properties of MSI tumor, it is recommended that CIN should be a supplementary biomarker. Studies are being pursued to determine if mixed MSI and CIN states alter immunotherapy response.

Tumor mutation burden is a frequently used biomarker that has recently been tested for its usage in immunotherapy response prediction; approximately 50% of TMB-high tumors still do not respond to immunotherapies [18]. Recently, a study was conducted of 67,000 patient samples including a thousand MSI-positive tumors [6]; the conventional definition of MSI was sufficient, but not necessary, for classification as elevated TMB. The Cancer Genome Atlas Network (n=276) also reported the same relationship between MSI and TMB [1], where 23% of hypermutated, TMB-high CRC tumors were tested negative for MSI, which included the six with the highest mutation rates. Such a case was also found in the samples. P592 CRC was obviously a MSS tumor from the targeted sequencing-based analysis, but had a TMB as high as the MSI tumors. In addition, from this tumor a low-level MSI was identified with sequencing, which were undetectable by a conventional PCR-CE tests, and a pathogenic MSH6 mutation with a low allelic fraction was identified. Thus, more sophisticated MSI NGS tests which consider other critical features such as CIN and clonal architecture may provide a more accurate predictor for determining patients who may respond to immunotherapy.

Figure 11:
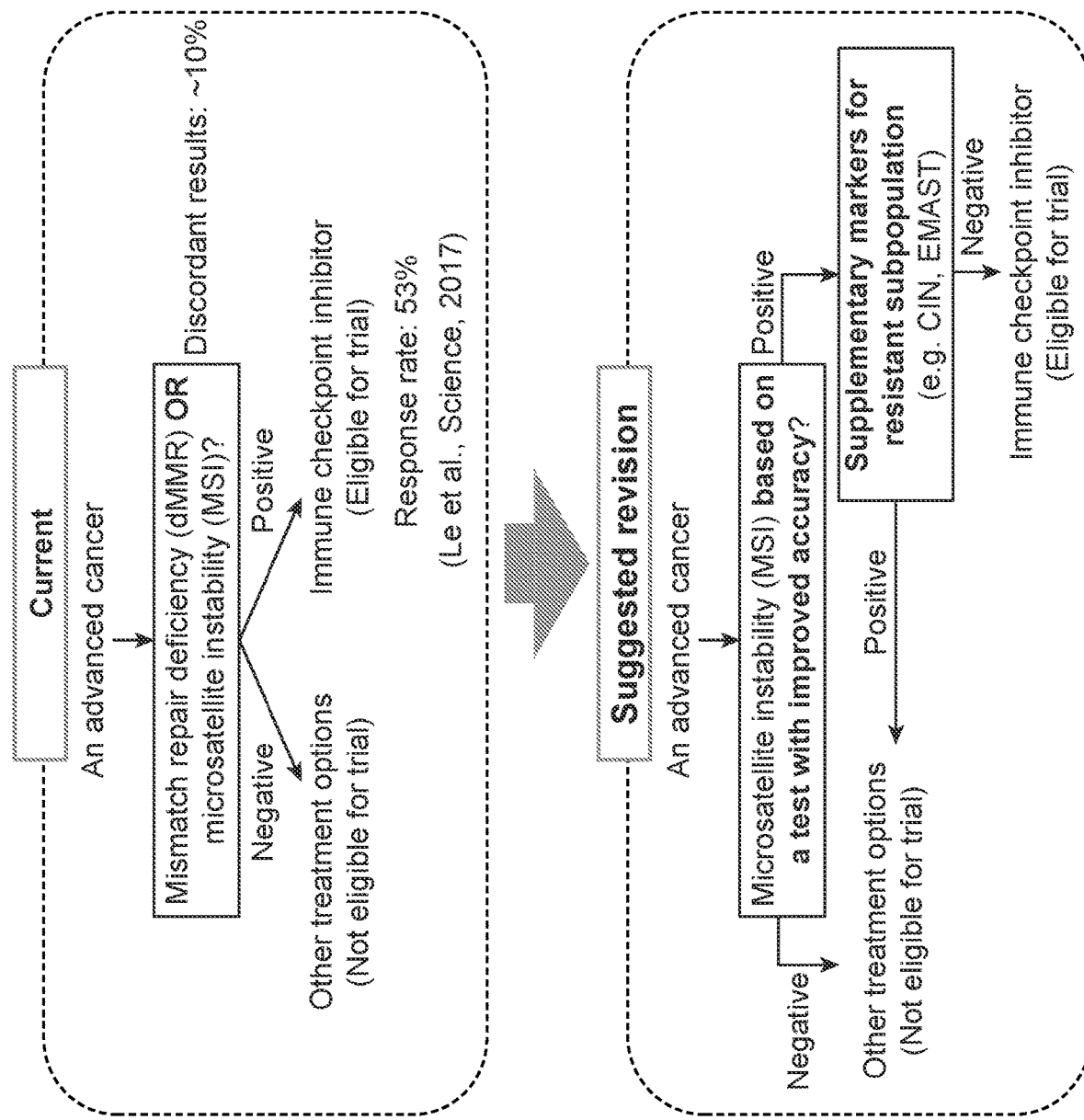
FIG. 11 provides current and suggested decision trees for cancer immunotherapy. Currently, a patient with an advanced cancer, regardless of tumor type, can be treated with an immune checkpoint inhibitor when positive from either tests for deficient mismatch repair (dMMR) or microsatellite instability (MSI). However, these tests are discordant in approximately 10% of all tested cases, and only half of the dMMR or MSI-positive tumors respond to the treatment. Based on the current study based on 46 CRCs, a revised decision tree for cancer immunotherapy is suggested here, where additional tests with supplementary markers to identify resistant subpopulations may improve prediction for the response.

Overall, this new sequencing approach determines MSI status based on all the microsatellite classes, CIN status and subclonal features. It was found that CIN phenotype was unexpectedly common in the MSI tumors, which suggest that evaluating CIN status may prove useful for determining immunotherapy response (FIG. 11). Other studies validated the conclusions. Chromosome 8 shows alterations in this context of MSI and CIN. In addition, the microsatellite frameshift at exon 7 of MSH3 and degree of EMAST were associated with the mixed phenotype. This analysis of highly multiplexed microsatellites provided better quantitative accuracy and distinguished MSI tumors with distinct characteristics in the mutation patterns in comparison to MSS tumors.

REFERENCES

1. Cancer Genome Atlas N: Comprehensive molecular characterization of human colon and rectal cancer. *Nature* 2012, 487:330-337.
2. Bacher J W, Flanagan L A, Smalley R L, Nassif N A, Burgart L J, Halberg R B, Megid W M, Thibodeau S N: Development of a fluorescent multiplex assay for detection of MSI-High tumors. *Dis Markers* 2004, 20:237-250.

3. Boland C R, Thibodeau S N, Hamilton S R, Sidransky D, Eshleman J R, Burt R W, Meltzer S J, Rodriguez-Bigas M A, Fodde R, Ranzani G N, Srivastava S: A National Cancer Institute Workshop on Microsatellite Instability for cancer detection and familial predisposition: development of international criteria for the determination of microsatellite instability in colorectal cancer. *Cancer Res* 1998, 58:5248-5257.
4. Cohen R, Hain E, Buhard O, Guilloux A, Bardier A, Kaci R, Bertheau P, Renaud F, Bibeau F, Flejou J F, et al: Association of Primary Resistance to Immune Checkpoint Inhibitors in Metastatic Colorectal Cancer With Misdiagnosis of Microsatellite Instability or Mismatch Repair Deficiency Status. *JAMA Oncol* 2019, 5:551-555.
5. Bartley A N, Luthra R, Saraiya D S, Urbauer D L, Broaddus R R: Identification of cancer patients with Lynch syndrome: clinically significant discordances and problems in tissue-based mismatch repair testing. *Cancer Prev Res (Phila)* 2012, 5:320-327.
6. Trabucco S E, Gowen K, Maund S L, Sanford E, Fabrizio D A, Hall M J, Yakirevich E, Gregg J P, Stephens P J, Frampton G M, et al: A Novel Next-Generation Sequencing Approach to Detecting Microsatellite Instability and Pan-Tumor Characterization of 1000 Microsatellite Instability-High Cases in 67,000 Patient Samples. *J Mol Diagn* 2019.
7. Cortes-Ciriano I, Lee S, Park W Y, Kim T M, Park P J: A molecular portrait of microsatellite instability across multiple cancers. *Nat Commun* 2017, 8:15180.
8. Hause R J, Pritchard C C, Shendure J, Salipante S J: Classification and characterization of microsatellite instability across 18 cancer types. *Nat Med* 2016, 22:1342-1350.
9. Middha S, Zhang L, Nafa K, Jayakumaran G, Wong D, Kim H R, Sadowska J, Berger M F, Delair D F, Shia J, et al: Reliable Pan-Cancer Microsatellite Instability Assessment by Using Targeted Next-Generation Sequencing Data. *JCO Precis Oncol* 2017, 2017.
10. Waalkes A, Smith N, Penewit K, Hempelmann J, Konnick E Q, Hause R J, Pritchard C C, Salipante S J: Accurate Pan-Cancer Molecular Diagnosis of Microsatellite Instability by Single-Molecule Molecular Inversion Probe Capture and High-Throughput Sequencing. *Clin Chem* 2018, 64:950-958.
11. Carethers J M: Microsatellite Instability Pathway and EMAST in Colorectal Cancer. *Curr Colorectal Cancer Rep* 2017, 13:73-80.
12. Watson M M, Lea D, Rewcastle E, Hagland H R, Soreide K: Elevated microsatellite alterations at selected tetranucleotides in early-stage colorectal cancers with and without high-frequency microsatellite instability: same, same but different? *Cancer Med* 2016, 5:1580-1587.
13. Torshizi Esfahani A, Seyedna S Y, Nazemalhosseini Mojarad E, Majd A, Asadzadeh Aghdaei H: MSI-L/EMAST is a predictive biomarker for metastasis in colorectal cancer patients. *J Cell Physiol* 2019, 234:13128-13136.
14. Chen M H, Chang S C, Lin P C, Yang S H, Lin C C, Lan Y T, Lin H H, Lin C H, Lai J I, Liang W Y, et al: Combined Microsatellite Instability and Elevated Microsatellite Alterations at Selected Tetranucleotide Repeats (EMAST) Might Be a More Promising Immune Biomarker in Colorectal Cancer. *Oncologist* 2019.
15. Wang Y, Vnencak-Jones C L, Cates J M, Shi C: Deciphering Elevated Microsatellite Alterations at Selected Tetra/Pentanucleotide Repeats, Microsatellite Instability, and Loss of Heterozygosity in Colorectal Cancers. *J Mol Diagn* 2018, 20:366-372.
16. Koi M, Tseng-Rogenski S S, Carethers J M: Inflammation-associated microsatellite alterations: Mechanisms and significance in the prognosis of patients with colorectal cancer. *World J Gastrointest Oncol* 2018, 10:1-14.
17. Ganesh K, Stadler Z K, Cercek A, Mendelsohn R B, Shia J, Segal N H, Diaz L A, Jr.: Immunotherapy in colorectal cancer: rationale, challenges and potential. *Nat Rev Gastroenterol Hepatol* 2019, 16:361-375.
18. Chan T A, Yarchoan M, Jaffee E, Swanton C, Quezada S A, Stenzinger A, Peters S: Development of tumor mutation burden as an immunotherapy biomarker: utility for the oncology clinic. *Ann Oncol* 2019, 30:44-56.
19. Le D T, Durham J N, Smith K N, Wang H, Bartlett B R, Aulakh L K, Lu S, Kemberling H, Wilt C, Luber B S, et al: Mismatch repair deficiency predicts response of solid tumors to PD-1 blockade. *Science* 2017, 357:409-413.
20. Walk E E, Yohe S L, Beckman A, Schade A, Zutter M M, Pfeifer J, Berry A B, College of American Pathologists Personalized Health Care C: The Cancer Immunotherapy Biomarker Testing Landscape. *Arch Pathol Lab Med* 2020, 144:706-724.
21. Hopmans E S, Natsoulis G, Bell J M, Grimes S M, Sieh W, Ji H P: A programmable method for massively parallel targeted sequencing. *Nucleic Acids Res* 2014, 42:e88.
22. Myllykangas S, Buenrostro J D, Natsoulis G, Bell J M, Ji H P: Efficient targeted resequencing of human germline and cancer genomes by oligonucleotide-selective sequencing. *Nat Biotechnol* 2011, 29:1024-1027.
23. Shin G, Grimes S M, Lee H, Lau B T, Xia L C, Ji H P: CRISPR-Cas9-targeted fragmentation and selective sequencing enable massively parallel microsatellite analysis. *Nat Commun* 2017, 8:14291.
24. Chalmers Z R, Connelly C F, Fabrizio D, Gay L, Ali S M, Ennis R, Schrock A, Campbell B, Shlien A, Chmielecki J, et al: Analysis of 100,000 human cancer genomes reveals the landscape of tumor mutational burden. *Genome Med* 2017, 9:34.
25. Chen T Q, Guestrin C: XGBoost: A Scalable Tree Boosting System. *Kdd'16: Proceedings of the 22nd Acm Sigkdd International Conference on Knowledge Discovery and Data Mining* 2016:785-794.
26. Cibulskis K, Lawrence M S, Carter S L, Sivachenko A, Jaffe D, Sougnez C, Gabriel S, Meyerson M, Lander E S, Getz G: Sensitive detection of somatic point mutations in impure and heterogeneous cancer samples. *Nat Biotechnol* 2013, 31:213-219.
27. Rentzsch P, Witten D, Cooper G M, Shendure J, Kircher M: CADD: predicting the deleteriousness of variants throughout the human genome. *Nucleic Acids Res* 2019, 47:D886-D894.
28. Li H, Durbin R: Fast and accurate short read alignment with Burrows-Wheeler transform. *Bioinformatics* 2009, 25:1754-1760.
29. Li H, Handsaker B, Wysoker A, Fennell T, Ruan J, Homer N, Marth G, Abecasis G, Durbin R, Genome Project Data Processing S: The Sequence Alignment/Map format and SAMtools. *Bioinformatics* 2009, 25:2078-2079.

30. Talevich E, Shain A H, Botton T, Bastian B C: CNVkit: Genome-Wide Copy Number Detection and Visualization from Targeted DNA Sequencing. *PLoS Comput Biol* 2016, 12:e1004873.
31. Cerami E, Gao J, Dogrusoz U, Gross B E, Sumer S O, Aksoy B A, Jacobsen A, Byrne C J, Heuer M L, Larsson E, et al: The cBio cancer genomics portal: an open platform for exploring multidimensional cancer genomics data. *Cancer Discov* 2012, 2:401-404.
32. Lee H, Flaherty P, Ji H P: Systematic genomic identification of colorectal cancer genes delineating advanced from early clinical stage and metastasis. *BMC Med Genomics* 2013, 6:54.
33. Bacher J W, Sievers C K, Albrecht D M, Grimes I C, Weiss J M, Matkowskyj K A, Agni R M, Vyazunova I, Clipson L, Storts D R, et al: Improved Detection of Microsatellite Instability in Early Colorectal Lesions. *PLoS One* 2015, 10:e0132727.
34. Umar A, Boland C R, Terdiman J P, Syngal S, de la Chapelle A, Ruschoff J, Fishel R, Lindor N M, Burgart L J, Hamelin R, et al: Revised Bethesda Guidelines for hereditary nonpolyposis colorectal cancer (Lynch syndrome) and microsatellite instability. *J Natl Cancer Inst* 2004, 96:261-268.
35. Xia L C, Van Hummelen P, Kubit M, Lee H, Bell J M, Grimes S M, Wood-Bouwens C, Greer S U, Barker T, Haslem D S, et al: Whole genome analysis identifies the association of TP53 genomic deletions with lower survival in Stage III colorectal cancer. *Sci Rep* 2020, 10:5009.
36. Liu Y, Sethi N S, Hinoue T, Schneider B G, Cherniack A D, Sanchez-Vega F, Seoane J A, Farshidfar F, Bowlby R, Islam M, et al: Comparative Molecular Analysis of Gastrointestinal Adenocarcinomas. *Cancer Cell* 2018, 33:721-735 e728.
37. Li L S, Kim N G, Kim S H, Park C, Kim H, Kang H J, Koh K H, Kim S N, Kim W H, Kim N K, Kim H: Chromosomal imbalances in the colorectal carcinomas with microsatellite instability. *Am J Pathol* 2003, 163:1429-1436.
38. Sinicrope F A, Rego R L, Halling K C, Foster N, Sargent D J, La Plant B, French A J, Laurie J A, Goldberg R M, Thibodeau S N, Witzig T E: Prognostic impact of microsatellite instability and DNA ploidy in human colon carcinoma patients. *Gastroenterology* 2006, 131:729-737.
39. Camps J, Armengol G, del Rey J, Lozano J J, Vauhkonen H, Prat E, Egozcue J, Sumoy L, Knuutila S, Miro R: Genome-wide differences between microsatellite stable and unstable colorectal tumors. *Carcinogenesis* 2006, 27:419-428.
40. Trautmann K, Terdiman J P, French A J, Roydasgupta R, Sein N, Kakar S, Fridlyand J, Snijders A M, Albertson D G, Thibodeau S N, Waldman F M: Chromosomal instability in microsatellite-unstable and stable colon cancer. *Clin Cancer Res* 2006, 12:6379-6385.
41. Chen W, Ding J, Jiang L, Liu Z, Zhou X, Shi D: DNA copy number profiling in microsatellite-stable and microsatellite-unstable hereditary non-polyposis colorectal cancers by targeted CNV array. *Funct Integr Genomics* 2017, 17:85-96.
42. Ali H, Bitar M S, Al Madhoun A, Marafie M, Al-Mulla F: Functionally-focused algorithmic analysis of high resolution microarray-CGH genomic landscapes demonstrates comparable genomic copy number aberrations in MSI and MSS sporadic colorectal cancer. *PLoS One* 2017, 12:e0171690.
43. Sveen A, Johannessen B, Tengs T, Danielsen S A, Eilertsen I A, Lind G E, Berg K C G, Leithe E, Meza-Zepeda L A, Domingo E, et al: Multilevel genomics of colorectal cancers with microsatellite instability-clinical impact of JAK1 mutations and consensus molecular subtype 1. *Genome Med* 2017, 9:46.
44. Cisyk A L, Nugent Z, Wightman R H, Singh H, McManus K J: Characterizing Microsatellite Instability and Chromosome Instability in Interval Colorectal Cancers. *Neoplasia* 2018, 20:943-950.
45. Roth A, Khattra J, Yap D, Wan A, Laks E, Biele J, Ha G, Aparicio S, Bouchard-Cote A, Shah S P: PyClone: statistical inference of clonal population structure in cancer. *Nat Methods* 2014, 11:396-398.
46. Schell M J, Yang M, Teer J K, Lo F Y, Madan A, Coppola D, Monteiro A N, Nebozhyn M V, Yue B, Loboda A, et al: A multigene mutation classification of 468 colorectal cancers reveals a prognostic role for APC. *Nat Commun* 2016, 7:11743.
47. Shin G, Greer S U, Xia L C, Lee H, Zhou J, Boles T C, Ji H P: Targeted short read sequencing and assembly of re-arrangements and candidate gene loci provide megabase diplotypes. *Nucleic Acids Res* 2019, 47:e115.
48. Bell J M, Lau B T, Greer S U, Wood-Bouwens C, Xia L C, Connolly I D, Gephart M H, Ji H P: Chromosome-scale mega-haplotypes enable digital karyotyping of cancer aneuploidy. *Nucleic Acids Res* 2017, 45:e162.
49. Greer S U, Nadauld L D, Lau B T, Chen J, Wood-Bouwens C, Ford J M, Kuo C J, Ji H P: Linked read sequencing resolves complex genomic rearrangements in gastric cancer metastases. *Genome Med* 2017, 9:57.
50. Xia L C, Bell J M, Wood-Bouwens C, Chen J J, Zhang N R, Ji H P: Identification of large rearrangements in cancer genomes with barcode linked reads. *Nucleic Acids Res* 2018, 46:e19.
51. Li Y, Pang X, Cui Z, Zhou Y, Mao F, Lin Y, Zhang X, Shen S, Zhu P, Zhao T, et al: Genetic factors associated with cancer racial disparity—an integrative study across twenty-one cancer types. *Mol Oncol* 2020.
52. Chen X, Wang J, Mitchell E, Guo J, Wang L, Zhang Y, Hodge J C, Shen Y: Recurrent 8q13.2-13.3 microdeletions associated with branchio-oto-renal syndrome are mediated by human endogenous retroviral (HERV) sequence blocks. *BMC Med Genet* 2014, 15:90.
53. Zare F, Dow M, Monteleone N, Hosny A, Nabavi S: An evaluation of copy number variation detection tools for cancer using whole exome sequencing data. *BMC Bioinformatics* 2017, 18:286.
54. Lee S Y, Chung H, Devaraj B, Iwaizumi M, Han H S, Hwang D Y, Seong M K, Jung B H, Carethers J M: Microsatellite alterations at selected tetranucleotide repeats are associated with morphologies of colorectal neoplasias. *Gastroenterology* 2010, 139:1519-1525.
55. Mandal R, Samstein R M, Lee K W, Havel J J, Wang H, Krishna C, Sabio E Y, Makarov V, Kuo F, Blecua P, et al: Genetic diversity of tumors with mismatch repair deficiency influences anti-PD-1 immunotherapy response. *Science* 2019, 364:485-491.
56. Plaschke J, Kruger S, Jeske B, Theissig F, Kreuz F R, Pistorius S, Saeger H D, Iaccarino I, Marra G, Schackert H K: Loss of MSH3 protein expression is frequent in MLH1-deficient colorectal cancer and is associated with disease progression. *Cancer Res* 2004, 64:864-870.

The invention claimed is:

1. A method for determining if a tumor has a mutation in a microsatellite, comprising:
   (a) isolating genomic DNA from a tumor sample and a non-tumor sample from the same patient to produce: i. a sample of tumor DNA and ii. a sample of non-tumor DNA, respectively;
   (b) without pre-amplifying the tumor or non-tumor DNA, sequencing a plurality of microsatellite loci from both the tumor and non-tumor DNA to provide sequence reads, wherein the sequenced microsatellite loci comprise mononucleotide, dinucleotide, trinucleotide and tetranucleotide microsatellites loci;
   (c) analyzing the sequence reads of (b) by:
      (i) determining a first profile of read counts across n alleles of a selected microsatellite locus in the tumor DNA; and
      (ii) using a Euclidean distance calculation to calculate the differences between the first profile of (i) and a second profile of read counts across n alleles for the selected microsatellite locus in the non-tumor DNA; and
      (iii) comparing the calculated difference to a threshold; and
   (d) designating the tumor as having mutation in the selected microsatellite locus if the difference of (ii) is equal to or above the threshold.

2. The method of claim 1, wherein step (b) is done by capturing, copying and sequencing the plurality of microsatellite loci from both the tumor and non-tumor DNA using OS-seq.

3. The method of claim 1, comprising:
   (e) repeating steps (c) and (d) for all of the sequenced microsatellite loci and
   (f) determining the number of microsatellite loci that have a mutation in the tumor DNA, thereby providing a measure of microsatellite instability in the tumor.

4. The method of claim 3, comprising:
   (g) identifying the patient as having a level of microsatellite instability that is above a threshold; and
   (h) administering immunotherapy to the patient.

5. The method of claim 4, wherein the immunotherapy is an immune checkpoint inhibitor.

6. The method of claim 5, wherein the immune checkpoint inhibitor is an anti-CTLA-4 antibody, an anti-PD1 antibody, an anti-PD-L1 antibody, an anti-TIM-3 antibody, an anti-VISTA antibody, an anti-LAG-3 antibody, an anti-IDO antibody, or an anti-KIR antibody.

7. The method of claim 1, wherein step (b) comprises copying and sequencing at least 100 microsatellite loci from both the tumor and non-tumor DNA.

8. The method of claim 1, wherein,
   step (b) further comprises: without pre-amplifying the tumor or non-tumor DNA, sequencing a plurality of unique non-microsatellite loci from both the tumor and non-tumor DNA to provide sequence reads, wherein the unique non-microsatellite loci comprise loci from all chromosomes;
   step (c) further comprises analyzing the sequence reads of a selected unique non-microsatellite locus by:
      (i) calculating the ratio of the total number of read counts for the selected unique non-microsatellite locus in the tumor DNA relative to the total number of read counts for the selected unique non-microsatellite locus in the non-tumor DNA; and
      (ii) comparing the ratio to a threshold; and
   step (d) further comprises designating the tumor as having chromosomal instability the ratio of (i) is equal to or above the threshold.

9. The method of claim 8, wherein the ratio is a normalized ratio.

10. The method of claim 8, wherein the ratio is a log 2 ratio.

11. The method of claim 8, wherein the sequencing of (b) is done by paired end sequencing and the sequence reads compared in step (c) are read 2 sequences.

12. The method of claim 11, wherein read 1 sequences are used to obtain read counts for individual microsatellite alleles after binning paired end reads based on read 2 sequences, where the first 40 bases from the 5' end work as a bin identifier.

13. The method of claim 8, wherein the plurality of unique non-microsatellite loci comprises at least 50 genes.

14. The method of claim 1, wherein n is in the range of 4-20.

* * * * *

SEQUENCE LISTING

<160> NUMBER OF SEQ ID NOS: 2

<210> SEQ ID NO 1
<211> LENGTH: 9
<212> TYPE: PRT
<213> ORGANISM: Homo sapien

<400> SEQUENCE: 1

Arg Ser Lys Val Thr Ala Leu Gly Phe
1               5

<210> SEQ ID NO 2
<211> LENGTH: 31
<212> TYPE: DNA
<213> ORGANISM: Homo sapien

<400> SEQUENCE: 2
ccatcgagat ttcactgtag ctagaccaaa a                              31